United States Patent
Laing et al.

(10) Patent No.: US 10,438,507 B2
(45) Date of Patent: Oct. 8, 2019

(54) HEALTH TRACKING SYSTEM INCLUDING SUBJECTIVE NUTRITION PERCEPTION TOOL

(71) Applicant: Under Armour, Inc., Baltimore, MD (US)

(72) Inventors: Scott Laing, Baltimore, MD (US); Daniel Townson, Baltimore, MD (US); Brian Carden, Baltimore, MD (US); Marcus Piña, Baltimore, MD (US); Gwen Johnson, Baltimore, MD (US); Allan Glen, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 273 days.

(21) Appl. No.: 15/130,716

(22) Filed: Apr. 15, 2016

(65) Prior Publication Data

US 2017/0301257 A1   Oct. 19, 2017

(51) Int. Cl.
| | |
|---|---|
| G09B 19/00 | (2006.01) |
| A61B 5/00 | (2006.01) |
| G09B 5/02 | (2006.01) |
| A61B 5/11 | (2006.01) |
| A61B 5/024 | (2006.01) |
| A61B 5/08 | (2006.01) |

(Continued)

(52) U.S. Cl.
CPC ........ *G09B 19/0092* (2013.01); *A61B 5/1118* (2013.01); *A61B 5/681* (2013.01); *A61B 5/6898* (2013.01); *A61B 5/7271* (2013.01); *A61B 5/7275* (2013.01); *A61B 5/7435* (2013.01); *G09B 5/02* (2013.01); *G16H 20/60* (2018.01); *G16H 40/63* (2018.01); *A61B 5/024* (2013.01); *A61B 5/08* (2013.01); *A61B 5/4806* (2013.01)

(58) Field of Classification Search
None
See application file for complete search history.

(56) References Cited

U.S. PATENT DOCUMENTS

| | | | | |
|---|---|---|---|---|
| 5,778,882 A | * | 7/1998 | Raymond | A61B 5/7435 600/513 |
| 6,314,405 B1 | * | 11/2001 | Richardson | A61B 5/0002 600/300 |

(Continued)

OTHER PUBLICATIONS

Food Journal; 2014; www.amazon.com/Love-Food-Exercise-Journal/dp/1449735502.*

*Primary Examiner* — Eddy Saint-Vil
*Assistant Examiner* — William D Ermlick
(74) *Attorney, Agent, or Firm* — Maginot, Moore & Beck LLP

(57) ABSTRACT

A health tracking system configured to provide activity, nutrition, health, and sleep data to a user. The health tracking system comprises a personal electronic device configured to receive health data obtained by a sensor device and/or manually input by the user and display personal metrics on a display screen. A subjective nutrition rating prompt is also provided to the user, which includes a plurality of simplified nutrition rating options, each of the simplified nutrition rating options providing a subjective nutrition consumption estimate. The personal electronic device is further configured to receive the simplified nutrition rating options input by the user and display nutrition estimate metrics on the display screen.

15 Claims, 11 Drawing Sheets

(51) Int. Cl.
*G16H 50/30* (2018.01)
*G16H 40/63* (2018.01)
*G16H 20/60* (2018.01)

(56) References Cited

U.S. PATENT DOCUMENTS

| | | | | |
|---|---|---|---|---|
| 7,311,666 | B2* | 12/2007 | Stupp | G06F 17/18 600/300 |
| 7,570,980 | B2* | 8/2009 | Ginsberg | A61B 5/14532 600/347 |
| 8,273,019 | B2* | 9/2012 | Crowley | G06Q 50/24 600/300 |
| 2001/0034730 | A1* | 10/2001 | Bhandari | G09B 5/00 |
| 2007/0238936 | A1* | 10/2007 | Becker | A61B 5/00 600/300 |
| 2008/0235232 | A1* | 9/2008 | Moses | G06Q 10/10 |
| 2009/0144089 | A1* | 6/2009 | Heywood | A61B 5/0002 705/3 |
| 2010/0003647 | A1* | 1/2010 | Brown | G09B 19/0092 434/127 |
| 2010/0022847 | A1* | 1/2010 | Crowley | G06Q 50/24 600/300 |
| 2010/0298899 | A1* | 11/2010 | Donnelly | A61B 5/02055 607/6 |
| 2011/0104648 | A1* | 5/2011 | Singer | G09B 19/00 434/236 |
| 2011/0195383 | A1* | 8/2011 | Weiss | G09B 19/0092 434/127 |
| 2011/0243392 | A1* | 10/2011 | Miyahara | G06Q 30/02 382/110 |
| 2012/0088212 | A1* | 4/2012 | Knaan | G09B 19/00 434/236 |
| 2013/0273509 | A1* | 10/2013 | Mutti | G09B 19/0092 434/127 |
| 2015/0036138 | A1* | 2/2015 | Watson | G01N 21/31 356/402 |
| 2015/0130830 | A1* | 5/2015 | Nagasaki | A61B 5/6898 345/592 |
| 2015/0324751 | A1* | 11/2015 | Orenstein | G06F 19/3481 702/3 |
| 2015/0325143 | A1* | 11/2015 | Gupta | G09B 19/00 434/127 |
| 2015/0339946 | A1* | 11/2015 | Pacione | A61B 5/411 434/236 |
| 2015/0339949 | A1* | 11/2015 | Landers | G09B 19/0092 434/127 |
| 2015/0356886 | A1* | 12/2015 | Kim | G09B 19/0092 434/127 |
| 2015/0364057 | A1* | 12/2015 | Catani | G09B 19/0092 434/127 |
| 2015/0371553 | A1* | 12/2015 | Vento | G09B 19/0092 434/127 |
| 2016/0066865 | A1* | 3/2016 | Ginsberg | A61B 5/14532 600/365 |
| 2016/0074707 | A1* | 3/2016 | Thorpe | G09B 19/0092 434/127 |
| 2016/0379520 | A1* | 12/2016 | Borel | G09B 19/0092 434/127 |
| 2017/0061821 | A1* | 3/2017 | Choi | G06K 9/00664 |
| 2017/0128007 | A1* | 5/2017 | Hayter | A61B 5/4866 |
| 2017/0132395 | A1* | 5/2017 | Futch | G06F 19/3481 |
| 2017/0323582 | A1* | 11/2017 | Nusbaum | G06F 19/3475 |

* cited by examiner

HEALTH TRACKING SYSTEM INCLUDING SUBJECTIVE NUTRITION PERCEPTION TOOL

FIELD

This document relates to the field health tracking. More particularly, the present disclosure relates to methods, systems, computer programs, and devices configured to enable collection and display of objective and subjective health information for a user.

BACKGROUND

Health tracking devices are increasingly utilized by individuals interested in tracking their personal health and fitness. These health tracking devices include, for example, heart rate monitors, step counters, stair counters, global positioning system ("GPS") tracking devices, so-called "smart" scales, as well as various other motion and biometric tracking devices. The popularity and increasing use of activity trackers creates vast amounts of data which may originate from disparate sources over long periods of time. As the data is collected over a period of time, the amount of data increases to a point where, it becomes difficult to present the data to the user in a logical and easy-to-comprehend format. Moreover, it is often difficult for the user to obtain practical information or feedback related to his or her health, fitness activities, and/or the effect of fitness activities on his or her health and general wellbeing.

Various display arrangements have been implemented in past devices which present raw health data to the user in a summarized format. Presentation of health data in raw numerical form or a chart format is common with current systems and devices. For example, a total number of steps for a given day may be presented to a user on a screen. The user may also be provided with a breakdown of steps over a given period of time (e.g., steps per hour for the past day, steps per day for the past week, etc.). While this information may be desired by the user, it is often difficult for the user to determine what effect such activity had upon his or her health and general wellbeing.

Some health tracking devices also include tools that allow the user to log nutritional data. However, using these tools is often difficult, as specific food items must be manually entered into the system by the user. Accordingly, entry of nutritional data into activity tracking systems has traditionally been time consuming and laborious. For this reason, many users do not take advantage of the nutritional logging capabilities of health tracking systems.

In view of the foregoing, it would be advantageous to provide health activity tracking system including a graphical user interface (GUI) which is configured to show a concise summary of numerous activity-related parameters for a given period of time. It would also be advantageous if the GUI were configured to allow the user to determine an effect that such activity had on his or her subjective health and general wellbeing. Moreover, it would be advantageous if the display included an intuitive dashboard presentation that allowed the user to determine associations between health and activity in a quick and convenient manner. It would also be advantageous if such a system included simplified nutritional logging capabilities for recording a user's subjective assessment of his or her nutrition.

SUMMARY

In accordance with one exemplary embodiment of the disclosure, there is provided a personal electronic device configured to provide health-related information to a user. The personal electronic device includes a receiver, a processor, and an interactive display screen. The receiver is configured to receive health data obtained by a sensor device and/or manually entered by the user. The processor is configured to execute a computer program comprising a plurality of instructions which are configured to, when executed, cause the processor to process said received health data into a plurality of personal metrics. The interactive display screen is configured to display the plurality of personal metrics, each of the plurality of personal metrics being associated with a period of time. The interactive display screen is further configured to display a nutrition rating prompt comprising a plurality of simplified nutrition rating options, each of the simplified nutrition rating options providing a nutrition consumption estimate based on a subjective observation of the user and associated with the period of time. The receiver is further configured to receive a selection of at least one of the simplified nutrition rating options by the user. The processor is further configured to generate nutrition estimate metrics based on the selection of the at least one of the simplified nutrition rating options by the user and cause the nutrition estimate metrics to be displayed on the interactive display screen Pursuant to another exemplary embodiment of the disclosure, a method is disclosed for presenting health data to a user. The method includes providing a nutrition rating prompt on a display screen of a personal electronic device, the nutrition rating prompt including a plurality of nutrition rating options, each of the nutrition rating options providing a nutrition consumption estimate associated with the period of time. The method further includes receiving a selection of one or more of the nutrition rating options from the user during the period of time. The selection is processed for presentation on the personal electronic device as nutrition estimate metrics for the user, each of the nutrition estimate metrics associated with the period of time. The nutrition estimate metrics for the user are displayed on the display screen of the personal electronic device.

In accordance with yet another exemplary embodiment of the disclosure, a non-transient computer readable medium contains instructions for controlling a personal electronic device. The instructions result in the personal electronic device providing a nutrition rating prompt on a display screen of the personal electronic device, the nutrition rating prompt including a plurality of selectable nutrition rating options, each of the nutrition rating options providing a nutrition consumption estimate associated with the period of time. A selection of one or more of the plurality of selectable nutrition rating options are received from a user during the period of time at the nutrition rating prompt. The selection of the one or more of the plurality of selectable nutrition rating options from the user are processed for presentation on the personal electronic device as nutrition estimate metrics for the user, each of the nutrition estimate metrics associated with the period of time. The nutrition estimate metrics for the user are displayed on the display screen of the personal electronic device.

The above described features and advantages, as well as others, will become more readily apparent to those of ordinary skill in the art by reference to the following detailed description and accompanying drawings. While it would be desirable to provide an activity tracking device and associated display that provides one or more of these or other advantageous features, the teachings disclosed herein extend to those embodiments which fall within the scope of the

All Figures © Under Armour, Inc. 2016. All rights reserved.

DESCRIPTION

Disclosed embodiments include systems, apparatus, methods and storage medium associated with health tracking in general, and in particular enabling collection and display of objective and subjective health information for a user.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Figure 1:
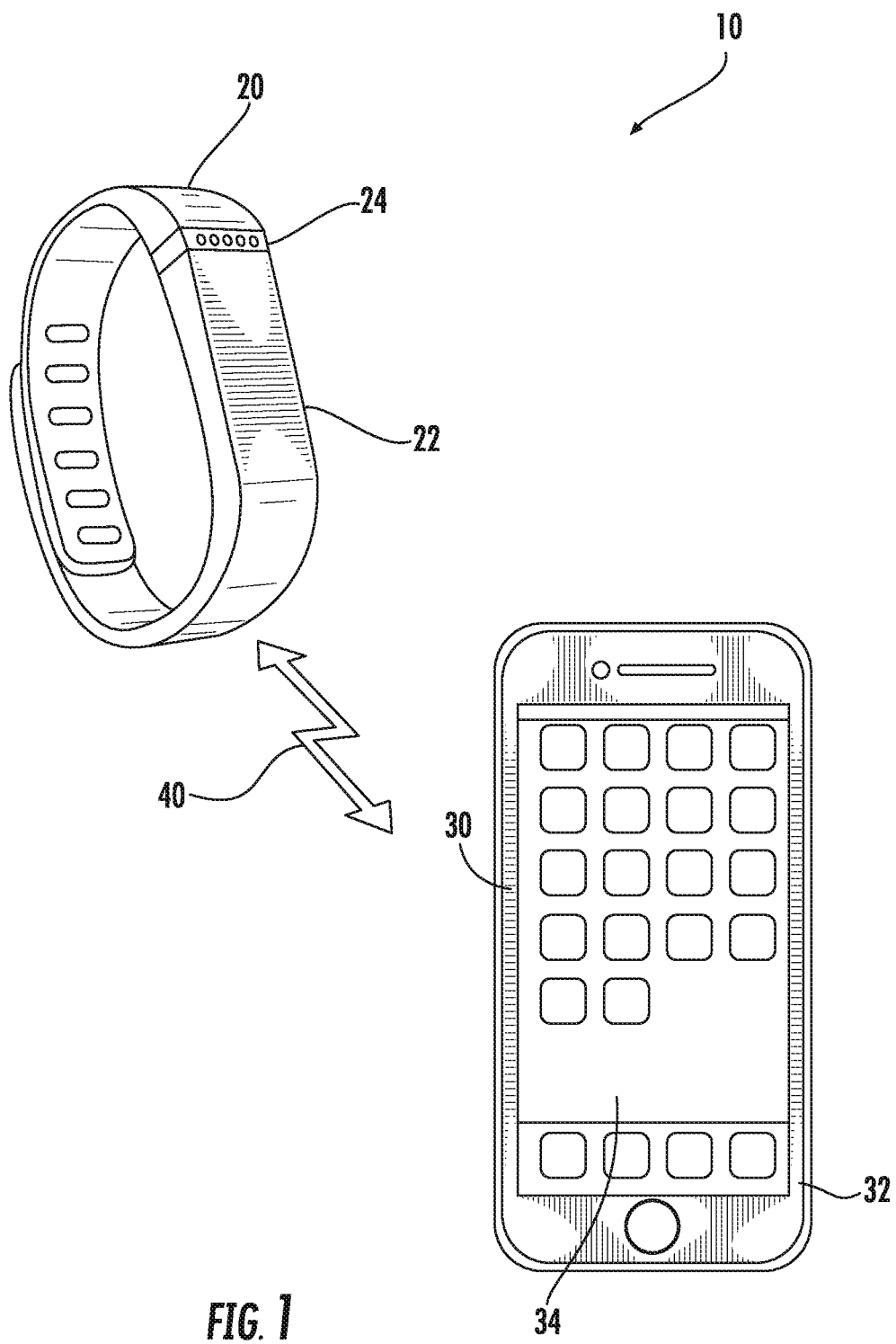
FIG. 1 is a diagrammatic view showing an exemplary embodiment of an activity tracking system including a sensor device and a display device.
Figure 2:
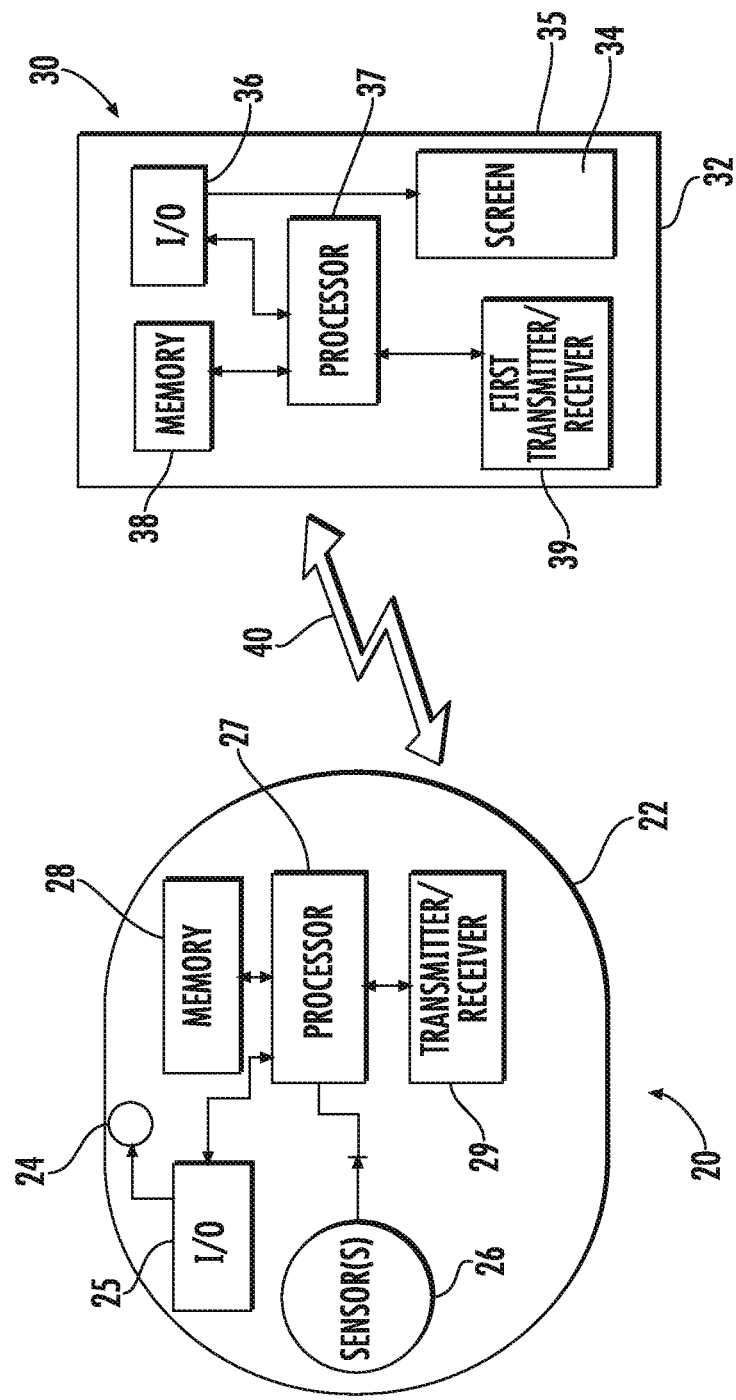
FIG. 2 is a block diagram of exemplary electronic components in the sensor device and the display device of the activity tracking system of FIG. 1.

With reference to FIGS. 1-2, an exemplary embodiment of a health tracking system 10 includes at least one health monitoring device 20 and an electronic display device 30 in communication therewith. The health monitoring device 20 is, in one embodiment, designed and dimensioned to be worn on or carried by the body of a user and collect activity information or other health information about the user. In another embodiment, the health monitoring device 20 may comprise a non-portable device configured to measure one or more health parameters of the user. For example, the device may measure the user's weight and/or nutrition. Moreover, an individual user may be associated to more than one health monitoring device 20 (as discussed in greater detail elsewhere herein). The health monitoring device 20 is in communication with the electronic display device 30, and is configured to deliver the collected data about the user to the electronic display device 30. The collected data may include activity data (e.g., measured in distance, steps, flights of stairs, etc.) or other health data. Examples of the collected data include sleep data, nutrition data, weight data, heart rate data, and other environmental data (including temperature, humidity, precipitation, altitude, etc.). The electronic display device 30 is designed to process the data and display it to the user in a format that shows context for daily exercise, general activity, and sleep behavior.

Health Monitoring Device

The health monitoring device 20 (which may also be referred to herein as a "health tracking device" or a "sensor device") may be provided in any of various forms and is configured to collect any of various types of health-related data related to a user. Such data may be, for example, human kinematic and/or physiological data that provides personal metrics information about a level of activity or type of activity during awake times, and sleep quality, amount, and/or other sleep information during sleep times. Accordingly, the health monitoring device 20 may be configured to collect one or more of step data, body motion data, distance traversal data, altitude data, heart rate data, body temperature data, breathing data, environmental/positional data (such that provided by a GPS receiver), food consumption data, or any of various other types of personal or environmental metrics that may be relevant to determining health parameters including awake time activities and/or sleep quantity and quality of the user. The term "health data" as used herein refers to data associated with the user during the user's wake time or sleep time, and such data may indicate the user's participation in any of various activities including eating, sleeping, high intensity activity, sedentary activity, and various degrees of activity in-between. Examples of health data include step data, body motion data, distance traversal data, altitude data, heart rate data, body temperature data, breathing data, environmental/positional data (such that provided by a GPS receiver), food consumption data, weight and/or body fat data, or any of various other types of personal metrics that may be relevant the user's health. The term "activity data" as used herein is a subset of health data, and refers to data related to physical activity (i.e., movement or lack thereof) of the user. Examples of activity data include step data, body motion data, distance traversal data, altitude data, heart rate data, breathing data, environmental/positional data (such that provided by a GPS receiver), or any of various other types of personal activity metrics that may be relevant the user's physical activity for a given period of time.

Health data may be collected via manual entry by the user, automatically by a sensor of the health monitoring device 20, and/or collected by any of various other means. The term "personal metric" as used herein refers to any of various measures of health data that may be defined by any of various parameters (e.g., user heart rate expressed as beats per minute, user activity defined by total steps for a day, distance traversed for some time period, calories spent, calories consumed, total time of activity, body weight, amount of body fat, sleep quality defined by sleep time and/or sleep quality/sleep cycles, any of the foregoing expressed as a percentage of a goal or other standard, etc.). In at least one embodiment, the health monitoring device 20 may be an activity tracker configured to measure one or more of steps taken (including walking or running), distance traversed, stairs climbed, heart rate, as well as various other personal metrics (such "activity trackers" are commonly also referred to as "fitness trackers"). These activity trackers may further process the measured parameter to determine other personal metrics such as calories spent, sleep quality, etc. Such further processing may occur on the activity tracker itself or in association with other computer devices in communication with the activity tracker. Additional or alternative examples of health-monitoring devices 20 include those sold under the trademarks FITBIT®, JAWBONE®, POLAR®, APPLE® and UNDER ARMOUR®.

In one exemplary embodiment the health monitoring device 20 is configured to be worn or carried by the human user. For example, in the embodiment shown in FIG. 1, the health monitoring device 20 is provided as a wrist band that the user straps to his or her wrist. However, it will be recognized that in other embodiments, the health monitoring device 20 may be provided in any of various different configurations to be worn on any of various locations on the body of the user, such as via a module that clips on to clothing, is worn on a chest strap, fits in a pocket of the user, and/or is incorporated into a garment or a shoe. Alternatively, the health monitoring device 20 may be fixed and non-portable device (i.e., not worn by the user), such as for example, a so-called smart scale onto which a user stands and/or a tablet or personal computing device into which the user enters health-related data, such as nutritional data. Additional examples of configurations for the s health monitoring device 20 include configurations where the sensor device is provided as a component of a multi-function device, such as a watch, a mobile phone or other personal electronic device. In the embodiment disclosed herein, the health monitoring device 20 is shown as being a completely separate unit from the display device 30. However, in at least one embodiment, the health monitoring device 20 and the display device 30 are provided as a single unit. For example, the health monitoring device 20 and the display device 30 may be provided as part of a mobile phone, so-called "smart" watch or other personal electronic device. While a single health monitoring device 20 is shown in the embodiment of FIG. 1, it will be recognized that multiple sensor devices may be used by a single user, each of the health monitoring device 20 configured for communication with the electronic display device 30.

With continued reference to the embodiment of FIGS. 1 and 2, the health monitoring device 20 includes a protective outer shell or housing 22 designed to retain and protect various sensors and other electronic components positioned within the housing 22. The housing 22 comprise any number of shapes, configurations, and/or materials, the description herein being merely exemplary. In at least one embodiment, the housing 22 includes a relatively rigid portion that securely retains the electronic components, and a more resilient portion which functions as an outer layer to provide shock absorption features in the event the health monitoring device 20 is dropped, falls, or otherwise withstands an amount of force. The health monitoring device 20 and housing 22 may be configured to be worn or otherwise carried by the user in any of a number of ways. For example, the housing 22 of the health monitoring device 20 may be provided as part of a chest or wrist strap having an associated clasp, or may include a clip or other arrangement that allows the health monitoring device 20 to be coupled to the clothing of the user (as discussed elsewhere herein).

The health monitoring device 20 may also include other features visible on the housing 22 such as an I/O interface 25, which may include a display 24, one or more connection ports (not shown), or other input and output hardware and software. The display 24 may vary based on the type of device. For example, in one embodiment the display 24 may simply be one or more colored lights and/or flashing patterns configured to communicate information to the user (e.g., progress towards a goal or other personal metric). In another embodiment, the display 24 may be an LCD or LED screen that provides more specific personal metric information to the user (e.g., total number of steps for the day, progress towards a goal, heart rate, some combination thereof, etc.). The connection ports may be used to connect the health monitoring device 20 to a power source or to share data with other electronic devices.

As shown in FIG. 2, the health monitoring device 20 includes electronic circuitry comprising one or more sensors 26 (optional), a processor 27, a memory 28, and a transceiver 29. The health monitoring device 20 also includes a battery or other power source (not shown) configured to power the various electronic devices within the health monitoring device 20. In at least one embodiment, the battery of the health monitoring device 20 is a rechargeable battery. In this embodiment, the health monitoring device 20 may be placed in or connected to a battery charger configured for use with the sensor module in order to recharge the battery.

In one embodiment, the health monitoring device 20 comprises one or more sensors 26. The sensors 26 may comprise any of various devices configured to collect the activity data, including step data, motion data, distance traversal data, GPS data, body weight data, altitude data, heart rate data, body temperature data, breathing data, environmental/positional data, or any of various other types of personal metrics that may be relevant to determining activities of the wearer. In at least one embodiment, the sensor is a 3-axis accelerometer configured to detect the steps of the wearer during walking and running, and general movements of the wearer during more sedentary periods such as sleep. Of course, it will be recognized by those of ordinary skill in the art that numerous other sensors may be used, depending on the type of activity the health monitoring device 20 is designed to detect.

With continued reference to FIG. 2, the processor 27 may be any of various microprocessors as will be recognized by those of ordinary skill in the art. The processor 27 is configured to receive data signals from the sensors 26, and other component parts of the health monitoring device 20 (such as data entered via the I/O input), and process such signals. The processor 27 is connected to the memory 28 and the transceiver 29, and may deliver processed data to one or both of the memory 28 and the transceiver 29. Additionally, the processor 27 may perform some processing on the received data prior to delivery thereof to the memory 28 or transceiver 29. For example, the processor 27 may associate the data with a particular time, day, user (in the instance that the device is configured to collect data relating to more than one user), and/or event. The processor 27 is also connected to the I/O interface 25, and may send signals to the I/O interface 25 which results in illumination of the display 24 in order to provide text and/or image based messages or otherwise communicate to the user.

The memory 28 is configured to store information, including both data and instructions. The data generally includes, e.g., health data, activity data, health-parameter data, etc. that may be retrieved from the processor 27. The instructions which are stored at the memory 28 generally include firmware and/or software for execution by the processor 27, such as a program that controls the settings for the sensor device, a program that controls the output of the display 24 on the health monitoring device 20, a program that controls the receipt of information via the sensor 26, a program that controls the transmission and reception of data via the transceiver 29, as well as any of various other programs that may be associated with the health monitoring device 20. Such instructions may be present on the device 20 at the time of manufacture or may be downloaded thereto via well-known mechanisms.

The memory 28 may be of any type capable of storing information accessible by the processor 27, such as a memory card, ROM, RAM, write-capable, read-only memories, or other computer-readable medium. The data may be stored in the memory 28 in a relational database as a table having a plurality of different fields and records, XML documents, or flat files. The data may also be formatted in any computer-readable format such as, but not limited to, binary values, ASCII or Unicode.

The transceiver 29 in one embodiment comprises an RF transmitter and receiver configured to transmit and receive communications signals over a short range using a wireless communications technology, such as Bluetooth®, using any of various communications protocols, such as TCP/IP. Such transceivers are well known and will be recognized by those of ordinary skill in the art. The transceiver 29 is particularly configured to communicate with the display device 30 when the health monitoring device 20 is within a given range of the display device 30, and transmit activity data to the display device 30.

While the health monitoring device 20 has been described herein as the primary device for collecting and transmitting health parameter data to the display device 30, it will be recognized that additional data may also be collected or otherwise obtained and/or input in to the display device 30 via various other mechanisms. In at least one embodiment, the user may manually input data into the health monitoring device 20 and/or the display device 30. For example, the user may manually collect sleep data or calorie consumption data and input such data into the health monitoring device 20 and/or the display device 30 without the use of a sensor and/or other device transmitting the activity data to the display device.

Display Device

With continued reference to FIGS. 1 and 2, in at least one embodiment, the display device 30 is a handheld computing device, such as a smartphone. The display device 30 generally includes an input/output interface 36, a processor 37, a memory 38, and a transceiver 39. While a smartphone has been shown as the display device 30 in FIGS. 1 and 2, it will be appreciated that the display device 30 may alternatively comprise any number of alternative devices. For example, the display device 30 may be a standalone device, such as a desktop PC or smart television. Alternatively, the display device may be any type of portable or other personal electronic device such as a watch, tablet computer, laptop computer, or any of various other mobile computing devices. As will be recognized by those of ordinary skill in the art, the components of the display device 30 may vary depending on the type of display device used. Such alternative display devices may include much (but not necessarily all) of the same functionality and components as the display device 30 shown in FIGS. 1 and 2, as well as additional functionality or components necessary for proper functioning thereof (not shown). In addition, the display device 30 may function as one of the one or more health monitoring devices 20 discussed elsewhere herein.

The display device 30 includes a protective outer shell or housing 32 designed to retain and protect the electronic components positioned within the housing 32. The housing 32 may comprise any number of shapes, configurations, and/or materials, the description herein being merely exemplary. In at least one embodiment, the housing 32 includes a relatively rigid portion that securely retains the electronic components, and a more resilient portion which functions as an outer layer to provide shock absorption features in the event the device 30 is dropped, falls, or otherwise withstands an amount of force. In embodiments wherein the display device 30 also functions as one or more health monitoring devices 20, the housing 32 may serve as a common housing for components of the display device 30 and components of the health monitoring device 20.

With continued reference to FIG. 2, the I/O interface 36 of the display device 30 includes software and hardware configured to facilitate communications with the one or more health monitoring devices 20 and/or communications to the user him/herself. The hardware includes a display screen 34 configured to visually display graphics, text and other data to the user. In particular, the display screen 34 of the I/O interface 36 is configured to display health-related data received from the health monitoring device 20. The hardware may also include a microphone and/or speakers to facilitate audio communications with the user and/or verbal entry of commands to the device 30. In at least one embodiment, the display screen 34 is a touch screen display that allows the user to see data presented on the display screen 34 and input data into the display device 30 via a keyboard on the touch screen.

It will be recognized that the health monitoring device 20 and the display device 30 may be provided as part of a health tracking system 10; the components of which are configured to communicate via e.g., a mobile telephony network, the Internet, and/or a global positioning system (GPS). In another embodiment, the methods, apparatus and systems disclosed in co-owned, co-pending U.S. patent application Ser. No. 14/853,221, filed on Sep. 14, 2015 and entitled "ACTIVITY TRACKING ARRANGEMENT AND ASSOCIATED DISPLAY WITH GOAL-BASED DASHBOARD", the entire contents of which are incorporated herein by reference, are utilized to perform at least certain ones of the herein discussed functionality.

The processor 37 of the display device 30 may be any of various processors as will be recognized by those of ordinary skill in the art. The processor 37 is connected to the I/O interface 36, the memory 38, and the transceiver 39, and is configured to deliver data to and/or receive data from each of these components. In at least one embodiment, the processor 37 is configured to process raw health-parameter data received from the one or more health monitoring devices 20 and transform the data into a graphical format for presentation on the display screen 34. It will be recognized by those of ordinary skill in the art that a "processor" as used herein includes any hardware system, hardware mechanism or hardware component that processes data, signals or other information. A processor can include a system with a central processing unit, multiple processing units, dedicated circuitry for achieving functionality, or other systems.

The memory 38 is configured to store information, including both data and instructions. The data may be, for example, health-parameter data as discussed above, which may be related to the activities, nutrition, sleep, environment, etc. of the user, along with other data that may be ancillary to the basic operation of the display device and any applications retained on the display device. The instructions which are stored at the memory 38 generally include firmware and other software for execution by the processor 37, such as a program that controls the settings for the display device, a program that controls the output of the display 34 on the display device 30, programs that control various applications on the display device, a program that controls the transmission and reception of data via the transceiver 39, as well as any of various other programs that may be associated with the display device 30. As explained in further detail below, the instructions stored in the memory 38 for execution by the processor may include, for example, an activity or health tracking app, a health perception tool, and/or a nutrition estimate tool.

The memory 38 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art.

In at least one embodiment, portions of the system and methods described herein may be implemented in suitable software code that may reside within the memory. Such software code may be present on the device 30 at the time of manufacture or may be downloaded thereto via well-known mechanisms. A computer program product implementing an embodiment disclosed herein may therefore comprise one or more computer-readable storage media storing computer instructions translatable by a processor to provide an embodiment of a system or perform an embodiment of a method disclosed herein. Computer instructions may be provided by lines of code in any of various languages as will be recognized by those of ordinary skill in the art. A "computer-readable medium" may be any type of data storage medium that can store computer instructions, including, but not limited to the memory devices discussed above.

The transceiver 39 is an RF transmitter and receiver configured to transmit and receive communications signals over a short range using a wireless communications technology, such as Bluetooth®, using any of various communications protocols, such as TCP/IP. Such transceivers are well known and will be recognized by those of ordinary skill in the art. The transceiver 39 is particularly configured to communicate with the transceiver 29 of the health monitoring device 20. The display device 30 also includes a battery or other power source (not shown) configured to power the transceiver 39 and various other the electronic components within the display device 30. In at least one embodiment, the transceiver 39 is configured to allow the display device 30 to communicate with a wireless telephony network, as will be recognized by those of ordinary skill in the art. The wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements.

Raw health data collected by the health monitoring device 20 may be processed by the display device 30 and/or delivered to a remote server for further processing. The processing to be performed may depend on various factors including the type of data received and different subscriptions of the user/athlete. Examples of such processing are provided in the paragraphs below.

Typical processing may relate to the user's current activity level, trends, history, training state, etc. For example, in one embodiment the one or more computers that processes the raw data may calculate an activity level which may be based on a combination of inputs, including, for example, steps taken over a period of time, heart rate, etc. In another embodiment, GPS data is used to determine various athletic data points, such as the speed of the athlete calculated over different time periods, total distance travelled, or the route taken by the athlete during a sporting event. Furthermore, the health data may be processed into different forms and formats, depending on the particular device that will ultimately be used to view the data. For example, the data may be processed into a first format that will allow it to be viewed on e.g., a smart watch and into a second format that will allow it to be viewed on the monitor of a personal computer; that is a compressed or summarized format for the smaller display and a more detailed format for the larger and more powerful display. Processing of health data may also depend on a subscription level the user maintains with the administrator of the health tracking system. If the user has a standard subscription with the administrator of the health tracking system 10, only limited processing may occur, such as an average heart rate for a period of time or a total number of steps for a day. However, if the user has a premium subscription with the administrator of the health tracking system, the processing of heart rate data may further include an analysis of the time the user spent in different heart rate zones during a given period of time, such as times in the fat burning zone, the aerobic zone, and the anaerobic zone. With respect to step data, users with premium subscriptions may receive detailed information about cadence, split times, or other in-depth analysis performed by the processor. While these are but a few examples of how the raw data may be processed by one or more computers of the health tracking system including the display device 30 or any remote servers, those of skill in the art will recognize that nearly countless other possibilities exist for systems and methods to process the data received from the one or more health monitoring devices 20 for subsequent viewing and analysis. After the raw activity data is transmitted and processed, the processed data may then be displayed or otherwise presented on a user interface of the display device 30.

In the instance a user carries one or more health monitoring devices 20, health data from each device 20 is delivered to the display device 30. As represented by the arrow 40 in FIGS. 1 and 2, the one or more health monitoring devices 20 are configured to transmit a wireless RF signal representative of the health data collected or obtained thereat to at least one display device 30. In addition, the health data may also be transmitted to additional computing devices (display devices 30), such as a watch or a laptop computer where the health data may be conveniently displayed for the user. In other embodiments, a wired connection may be utilized for communication of health data between the display device 30 and the health monitoring device 20.

In another embodiment, the transmission of data from the health monitoring device 20 to the display device 30 occurs automatically without the user needing to prompt the transmission. Because the transmissions in this embodiment are automatic, some mechanism may be used to turn on the transceiver 29 of the health monitoring device 20 or otherwise indicate that automatic transmissions should begin. For example, in one embodiment, an on/off switch is provided on the health monitoring device 20 that allows the athlete or user to begin automatic transmissions of data from the health monitoring device 20. In another embodiment, the health monitoring device 20 may be configured to begin transmissions once it receives a confirmation that the display device 30 is within an appropriate range of the health monitoring device 20. In yet another embodiment, data transmission may occur periodically at predetermined intervals of time. In other embodiments, where communications between the health monitoring device 20 and the display device 30 are made with a wired connection, communications only occur when the wired connection is established between the health monitoring device 20 and the display device 30.

The health data transmitted to the display device 30 is processed to determine one or more personal metrics for the user. As noted above, any of various personal metrics may be presented depending on the activity data or other health data collected by the health monitoring device 20. For example, the personal metrics may include, heart rates, awake times, sleep times, total steps, intensity level, sleep quality, calories spent, weight, body fat percentage, etc. The personal metrics may provide instantaneous activity information (e.g., current heart rate) or activity information determined over a given period of time (e.g., average heart rate). If the activity data indicates that the user is walking or running, the appropriate processor 27 or 37 may determine that the user is participating in a high intensity awake activity and/or may calculate a value for the intensity level. On the other hand, if the activity data indicates that the user is sitting or generally sedentary, the appropriate processor 27 or 37 may determine that the user is participating in a lower level awake activity. In at least one embodiment, the activity data may indicate that the user is sleeping or has retired to bed for an evening. In another embodiment, the user may indicate on the health monitoring device 20 and/or on the display device 30 that he or she has retired to bed (e.g., by making an appropriate selection on the device 20 or 30). During these times, the appropriate processor 27 or 37 may determine a quality of sleep of the user by determining activity levels during sleep. Relatively low movement and/or low heart rate during sleep may indicate deeper sleep levels and significant movement during sleep and/or increased heart rate may indicate lighter sleep or even additional awake times. When the user awakens the following morning, the appropriate processor 27 or 37 may automatically determine based on the activity signals that the user has awakened from his or her sleep and is participating in activities of various intensities.

After the activity data or other health data is processed to determine one or more personal metrics for the user, the processor 37 may further process the health data in order to present the health data in a format for quickly and easily communicating the collected health data to the user. To this end, the processor is configured to communicate with the I/O interface 36 and cause display of the processed activity or health information on the screen 34 for viewing by the user. One exemplary format in which the personal metrics are presented to the user via the display are described in further detail below with reference to FIGS. 3A-3C.

Display of Goal-Based Health Data in Sector Form

Figure 3A:
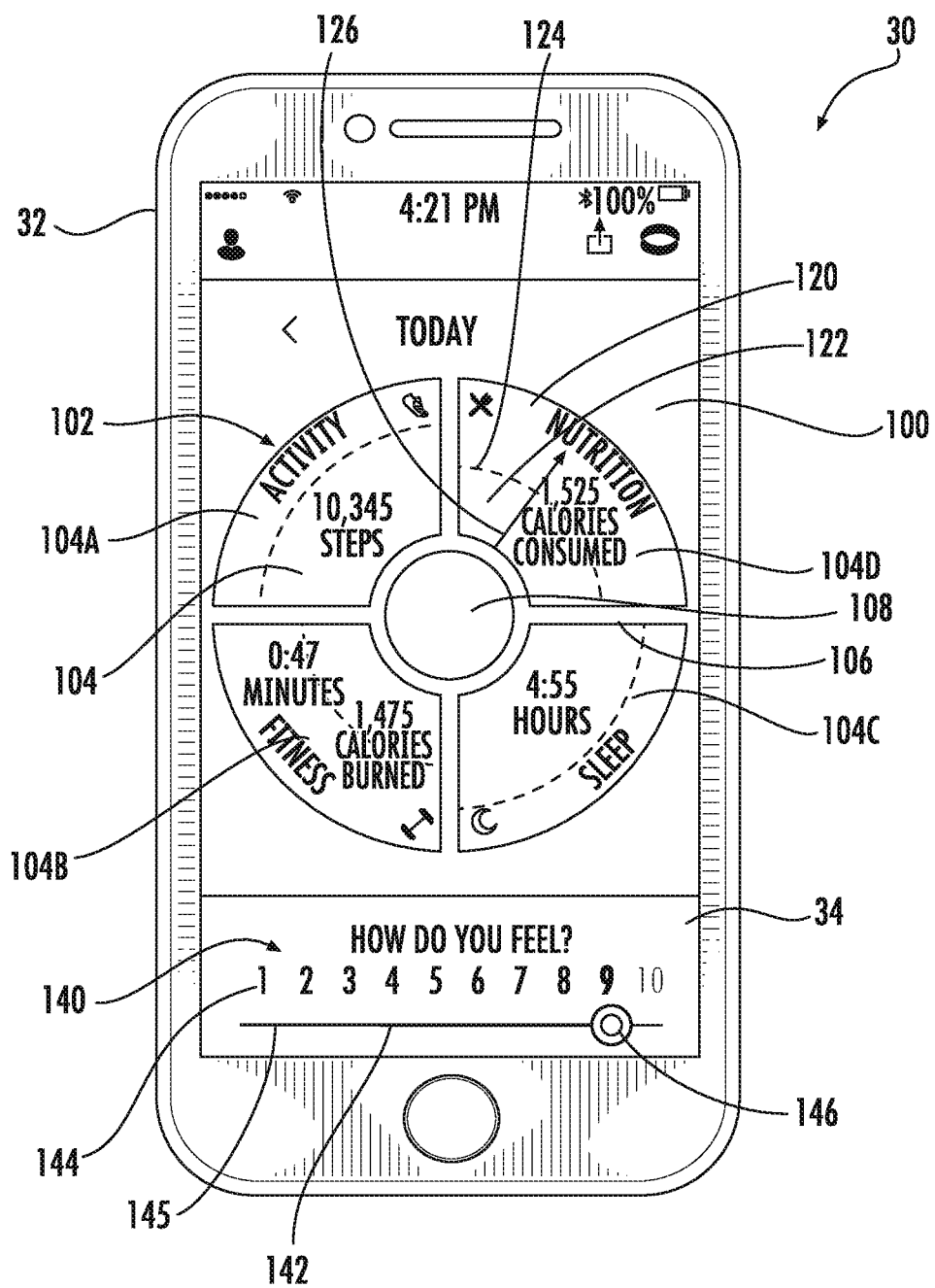
FIG. 3A is a plan view showing the display device of the activity tracking system of FIG. 1 including a dashboard screen displayed on the display device, the screen including activity data for a user obtained by the sensor device and a health perception prompt.

With reference now to FIG. 3A, a display device 30 is shown in the form of a mobile telephone. The display device 30 includes a screen 34 configured to display the processed health data obtained from the health monitoring device 20 and/or input manually by the user. The health data on the screen 34 is, in one embodiment, processed and displayed using an activity tracking software application or "app" stored in a computer readable medium such as the memory 38 of the display device 30. The processor 37 of the display device is configured to process the instructions for the app, which may be downloaded thereto such as via a so-called "app store" or application store, and provide a graphical user interface, including various screens disclosed herein with reference to FIGS. 3A-4C.

FIG. 3A shows a dashboard screen 100 of the activity or health tracking app. The dashboard screen 100 provides the user with a brief overview of health data for a period of time, such as a day. The dashboard screen 100 also serves as an entry point for the user to obtain more detailed information concerning various health data provided on the dashboard screen. In the embodiment disclosed herein, the dashboard screen 100 serves as the home screen for the activity or health tracking app.

As shown in FIG. 3A, the dashboard screen 100 includes a chart 102 in the form of a wheel divided into a plurality of sectors 104, including sectors 104A-104D. The sectors 104 in the embodiment of FIG. 3A are circular sectors, each sector provided as a quadrant of the wheel. Each sector 104 is positioned between two adjacent sectors (e.g., sector 104B is positioned between adjacent sector 104A and 104C). Linear gaps divide each of the adjacent sectors 104. A central hub 108 is provided at the center of the chart 102, and each of the linear gaps 106 extends radially away from the central hub 108. The central hub 108 may display additional data related to the user or a link to such additional data, such as a user weight, heart rate, profile data, or other data related to or of interest to the user.

Each sector 104 of the wheel is associated with an activity or health parameter and displays a personal metric 130 for the user. In the embodiment of FIG. 3A, sector 104A is associated with steps for the day, sector 104B is associated with active minutes (e.g., time participating in fitness activities) as well as calories burned for the day, sector 104C is associated with sleep time for the day, and sector 104D is associated with calories consumed for the day. The activity or health parameter associated with each sector 104 may be displayed in one or more ways. For example, the "steps" activity parameter in sector 104A is represented with both text (i.e., "steps") and an icon (i.e., the shoe icon). In at least one embodiment, each of the different sectors 104 is represented on the chart by a different color to further illustrate that each sector is associated with a different activity or health parameter (e.g., sector 104A may be a different color from each of sectors 104B, 104C and 104D).

As noted above, a personal metric 130 is also displayed in association with each sector 104. In the embodiment of FIG. 3A, the user's personal metric 130 for sector 104A is "10,345" steps, the user's personal metric for sector 104B is "0:47" active minutes (i.e., forty-seven active minutes) and 1,475 calories burned, the user's personal metric for sector 104C is "4:55" hours of sleep (i.e., four hours and fifty-five minutes of sleep), and the user's personal metric for sector 104D is "1,525" calories consumed.

In addition to expressing the personal metric 130 for each sector 104 in raw numerical form, the personal metric for each sector may also (or alternatively) be expressed in other forms. For example, the personal metric may be expressed numerically or graphically as a progress toward a goal (which goal may be defined in different ways, such as a desire to exceed some value for a particular activity or health parameter or fall short of some value for another activity or health parameter). This progress may be shown in different ways, such as numerically as a fraction or a percentage of the goal. Alternatively, this progress may be shown graphically.

In the embodiment of FIG. 3A, the personal metric is expressed graphically as progress toward a goal. For example, as can be seen with reference to sector 104D of FIG. 3A, the sector 104D is split into a first section 120 and a second section 122. The first section 120 has a first color, and the second section 122 has a second color that is different from the first color (e.g., the first section 120 may be white while the second section 122 may have a significant gray tint). A boundary 124 exists between the first section 120 and the second section 122. This boundary 124 is may be provided by a defined line or may simply be represented by the color transition between the first section 120 and the second section. The entire sector 104D represents the user's goal for the health parameter for the day (e.g., consume less than 3,000 calories). The area of the first section 120 represents the user's progress toward the user's goal for the day. The numerical value "1,525" in the sector 104D displays the personal metric toward that goal at the time. The area in the second section 122 represents what remains for the user to achieve the goal. In this case, if the user's goal is to consume less than 3,000 calories for the day, the user's progress is 1,525 calories consumed, which is about ½ of the way to the goal. Accordingly, the first section 120 extends outwardly from the central hub 108 about ½ of the distance to the outer perimeter edge of the sector. Alternatively, the first section 120 may be shown as filling about ½ of the total area of the sector 104D. Similar logic applies to the other ones of the user's goals displayed on the dashboard 100.

With continued reference to sector 104D of FIG. 3A, as additional calories are consumed by the user, the area of the first section 120 is increased, and the area of the second section 122 is decreased. In other words, for each additional calorie consumption logged by the user, the boundary 124 between the first section 120 and the second section 122 moves radially outward from the central hub 108 in the direction of arrow 126, indicating progress toward a goal. In this manner, the sectors 104 of the chart 102 provide personal metrics as not only raw numerical data but also graphically as progress toward a goal. While progress toward a goal has been described in FIG. 3A by the boundary 124 moving in the direction of arrow 126, it will be appreciated that the boundary may also move in a different manner, such as toward the central hub 108. As another example, the boundary 124 may be radially-oriented and may move in a circumferential direction (instead of a circumferential boundary moving in a radial direction as shown in FIG. 3A). As another example, movement toward a goal may simply be expressed in each sector as a percentage (e.g., "½ to goal" shows progress of about half the way to the stated goal).

While sector 104D shows an example of a goal where the user wishes to fall short of some measurement for an activity or health parameter, it will be recognized that in other sectors, the user's goal may be to surpass a measurement for the activity or health parameter. For example, sector in 104A, the user's goal may be to surpass 14,000 steps for the day, and the user has logged over ⅔ of the steps necessary to achieving that goal. As another example, in sector 104B, the user's goal may be two hours of physical activity for the day, and the user has yet to log half the time required to achieve that goal. As yet another example, in sector 104C, the user's goal for the day may have been to obtain seven and a half hours of sleep, and the user achieved that goal overnight. Because the user achieved the goal illustrated in sector 104C, the sector is completely one color (i.e., white), indicating that the goal has been achieved. However, as noted previously, in other embodiments the progress toward a goal may be stated differently, such as a percentage toward completing a goal (e.g., "100% of goal achieved").

In another embodiment, when the user exceeds a goal, a new goal may be provided for the user which is an incremental increase over previous goals. In a further example, additional badges, colors, messages, animations, etc. may be provided when a user exceeds a goal.

As described above, the health parameter data obtained by the health monitoring device 20 for the user is provided in sector form on the dashboard screen 100. In particular, the dashboard screen 100 includes a chart 102 that is divided into a number of sectors 104, each of the sectors 104 representing an activity parameter. While the chart 102 is a circular or pie-chart in the embodiment of FIG. 3A, it will be recognized that the chart may be provided in other forms. For example, the chart may be provided as a square chart, oval chart, rectangular chart, or in any of various other shapes with any of various sizes. Similarly, while the sectors 104 in the embodiment of FIG. 3A are shown as circular sectors, it will be recognized that the sectors 104 may be provided in different forms. For example, the sectors may be provided on a square chart and the quadrants may be defined by triangular shapes, square shapes. Additionally, while the sectors are disclosed in the embodiment of FIG. 3A as being quadrants, it will be recognized that the sectors may also be different portions of the associated chart. For example, the sectors may define sextants or octants within the chart. Accordingly, it will be recognized that FIG. 3A shows but one exemplary representation of health data provided in sector form, and numerous variations of the display of health data in sector form are possible and contemplated herein.

Health Perception Prompt

With continued reference to FIG. 3A, the lower portion of the screen 34 below the chart 102 includes a health perception prompt 140 configured to receive health perception data input by the user. The health perception prompt 140 of the dashboard includes a sliding scale 142 with a series of numbers 144 positioned along a bar 145, and a marker 146 on the bar 145, the series of numbers providing a range of values for the user. The sliding scale 142 allows the user to touch a marker 146 on the screen 34 (and/or slide the marker) and move the marker between a low number (e.g., "1") indicating that the user does not feel well, and a high number (e.g., "10") indicating that the user feels very well. The health perception prompt 140 is configured to be a subjective indication of how the user feels on a particular day. Accordingly, different users may view the health perception prompt differently. For example, some user will base entries at the health perception prompt based only on physical wellness, while others may base entries at the health perception prompt on physical and psychological wellness. Also, because pain, wellness and related scoring evaluation are subjective in nature, one user's seven rating may be another user's three. Therefore, it will be appreciated that the entries at the health perception prompt 140 are as perceived by an individual user, not by a third party. The term "health perception" as used herein refers to a personal feeling or subjective perception of one's own health as determined by the user himself or herself based on the user's own senses, feelings, awareness, mental impressions, or other perceptions of the user. As used herein, a subjective "health perception" is in contrast to a "health diagnosis" that is a more objective analysis of the health condition of the user based on the identification of symptoms of the user, physical or mental examinations of the user, analysis of biological, physical or mental tests on the user, and/or any conclusions resulting therefrom. Similarly, the term "health perception metric" as used herein refers to any of various measures of health perception (e.g., in the embodiment of FIG. 3A, a value between one and ten).

In at least one embodiment, the user may move the health perception prompt any number of times during the day, but only a single entry will be saved in association with each day. For example, the health tracking app may only save the first or the final entry at the health perception prompt 140 for any given day. In another embodiment, the user may move the health perception prompt several times during the day, and multiple entries will be saved for the day, depending on any of a number of different events or triggers. For example, the health tracking app may save a first and a final entry, the entry closest to one or more times (e.g., 8:00 am, noon, 8:00 pm, etc.), the first entry immediately after a workout, etc. Alternatively, if multiple entries are entered for a day, the health tracking app may save an average of such entries, or some limited number of entries for the day.

Figure 3B:
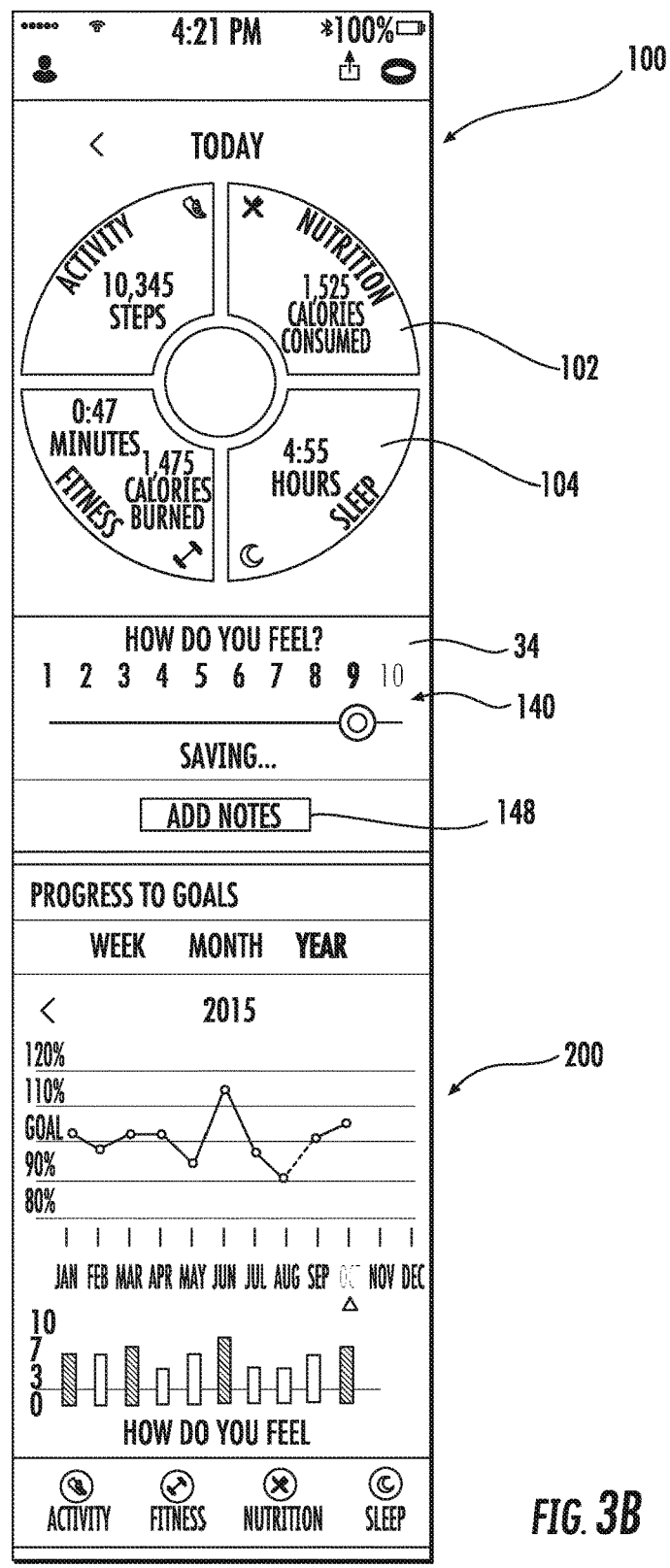
FIG. 3B is a plan view showing an extended version of the dashboard screen of FIG. 3A, the screen further including a personal metrics and health perception tool.

With reference now to FIG. 3B, an extended dashboard screen is shown, including the screen of FIG. 3A at the top portion as well as additional portions of the screen that the user may view. In one embodiment, the additional portions are viewed by the user scrolling down (e.g., by touching the screen and moving his or her finger in an upward direction to pull the bottom portion of the screen upward) and/or selecting an icon or button on the dashboard screen 100. These additional portions of the screen include a user notes option 148, and an output screen 200 of a personal metrics and health perception tool (described below with reference to FIGS. 3B and 3C). By touching the user notes option 148, the user is presented with a notes box (not shown). The user may then enter text in the notes box (e.g., by typing or speaking) which will allow the user to note why he or she is feeling a certain way. For example, if the user indicates a relatively high score for feeling on the health perception prompt 140, the user may indicate why he or she feels this way. These reasons may or may not be health related, and may be reviewed at a future time to assist the user in determining why he or she felt a certain way on a particular day (e.g., "just ran five miles," "lots of energy after a salad with grilled chicken for lunch," or "just had a great conversation with mom").

In at least one embodiment, when the user slides the marker 146 below a threshold (e.g., any number below "5") detail boxes (not shown) appear, providing the user with specific options to explain his or her feelings. The detail boxes are each associated with a perceived physiological condition related to health, wellness or feelings (e.g., tired, headache, stomach, allergies, muscle soreness, stress, lazy feeling, hung-over, etc.). The detail boxes are toggle boxes allowing the user to touch the box and mark that the condition is perceived by the user as a factor in his or her overall health at the time. In at least one embodiment, the detail boxes change depending on the number selected by the user on the sliding scale 142. For example, if a number below five is chosen, the detail boxes associated with bad feelings and poor health may be displayed; if a number of five or greater is chosen, the displayed detail boxes may be associated with different physiological conditions that may be perceived by the user (e.g., energetic, happy, rested, relaxed, strong, etc.). In at least one embodiment, the detail boxes associated with a perceived physiological condition are different depending on the number selected, however some of the detail boxes may be associated with more than one number (e.g., the "tired" detail box may be associated with each of numbers 1-5, and the "relaxed" detail box may be associated with each of numbers 5-10). In other embodiments, additional questions may be presented to the user depending on the detail box checked by the user (e.g., "how sore are you", "how stressed are you", "how much energy do you have"), and each of these questions may be associated with a sliding scale. The entries for these perceived feelings may be processed as part of the data analytics to arrive at the health perception metrics (e.g., feeling very sore may not be weighed as heavily as feeling lethargic). Moreover, it will be recognized that the while the embodiment of the health perception prompt 140 disclosed herein allows the user to input health perception data using the sliding scale 142, in other embodiments health perception data may be input by the user in different manners and in different forms. Furthermore, even if the health perception prompt includes a scale, the scale may be arranged differently than that shown in FIGS. 3A and 3B. Accordingly, while one embodiment of the health perception prompt 140 of the dashboard screen 100 is shown and described herein, it will be appreciated that various embodiments of the health perception prompt 140 and methods for entry of related health perception data are possible.

Personal Metrics and Health Perception Tool

Figure 3C:
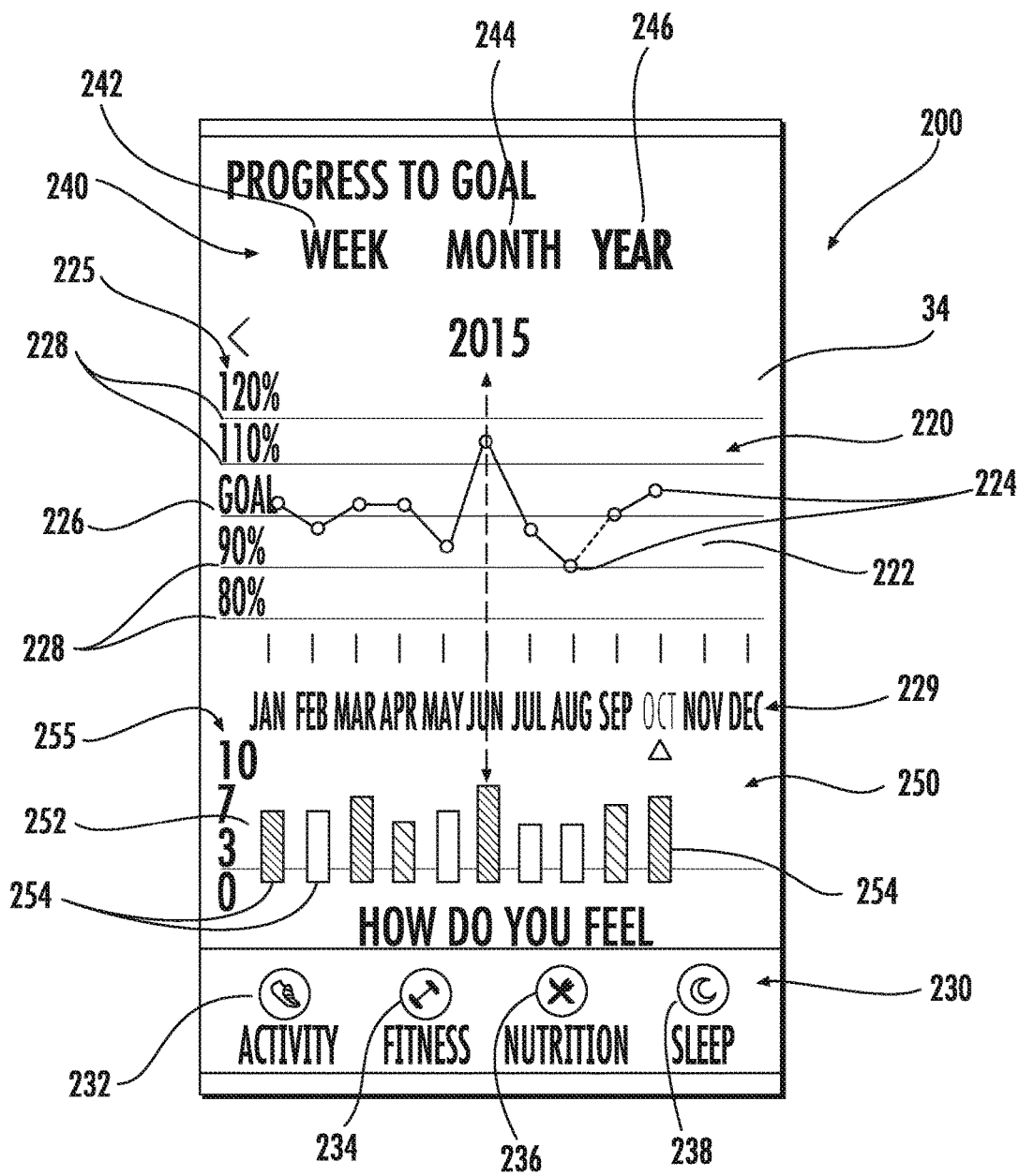
FIG. 3C is a plan view showing an enlarged view of the bottom portion of the dashboard screen of FIG. 3B.

With reference now to FIGS. 3B and 3C, the personal metrics and health perception tool (which may also be simply referred to herein as a "health perception tool") includes the health perception prompt 140 as well as an output screen 200 which provides the user with an easy and convenient means for determining whether particular activities result in or associated with particular feelings or perceptions. The health perception tool is stored as instructions in the memory 38 of the display device 30 and is configured for execution by the processor 37. Such instructions may be present on the device 20 at the time of manufacture or may be downloaded thereto via well-known mechanisms.

The health perception tool may be part of the activity or health tracking app, or may comprise a separate app used in association therewith; instructions for performing the herein disclosed functionality may be stored in the memory 38 of the display device 30. As best shown in FIG. 3C, the output screen 200 of the health perception tool includes both a personal metrics portion 220 and a health perception portion 250. In at least one embodiment, the health perception prompt 140, described above, may be configured as part of the health perception tool. In such an embodiment, the health perception prompt 140 provides an input portion of the tool and the output screen 200 provides an output and analysis portion of the tool.

With continued reference to FIG. 3C, the personal metrics portion 220 provided by the health perception tool generally provides the user with personal metric information based on activity or health data for the user. The activity or health data used to derive each personal metric in the personal metrics portion 220 may be obtained in any of various manners such as using one or more sensor devices 20 or via manual input by the user. Each of the personal metrics is associated with a given period of time.

In the embodiment of FIG. 3C, the personal metrics portion 220 is provided by a personal metrics graph 222 showing activity or health data over a period of time. Each personal metric data point 224 on the graph 222 is expressed as a percentage of a goal. For example, a goal for the user may be a number of steps per day (e.g., 7,000 steps per day). This daily goal is then translated into a period of time associated with the graph 222 (e.g., weeks, months or year). In the embodiment of FIG. 3C, the user has selected to view activity or health data for the year (i.e., calendar year 2015), and each personal metric is expressed as a percentage of a goal for one month of the year. Data points 224 for each personal metric are defined by (i) a y-coordinate indicating a value on the y-axis 225 of the chart 222, and (ii) an x-coordinate indicating a value on the x-axis 229 of the chart 222. Ten personal metrics data points 224 are displayed in the graph 222 (i.e., a personal metric for each of the months of January through October; no personal metric is presented for the remaining months of the year, November and December).

The system 10 automatically translates the user's daily goal of 7,000 steps per day into a monthly goal. This translation may be accomplished in any number of ways, such as a calculating a total number of steps for the month and determining whether the user achieved the total number of steps (e.g., 7,000 goal-steps/day×31 days/month=217,000 goal-steps/month). The graph includes a goal line 226, and a number of related goal percentage lines 228 (e.g., 80%, 90%, 110%, 120% of the goal, etc.). The personal metrics portion 220 of the graph 222 provides a plot of each personal metric data point for the associated period of time (e.g., month).

As shown in FIG. 3C, the personal metrics portion 220 allows the user to quickly and easily determine a personal metric for a period of time. In the example of FIG. 3C, a review of the graph shows that the user was relatively close to the goal (and in some instances exceeded the goal) in the months of January, February, March, April, July and September. In the months of June and October, the user significantly exceeded the goal. In the months of May and August, the user fell significantly short of the goal (i.e., closer to 90% of the goal). In this manner, a user can quickly and easily determine personal metrics associated with a given period of time, such as whether the user reached a particular goal for a month. In a further embodiment, the user may enter a precise date range within which the health data is to be displayed as discussed herein.

It will be recognized that different types of personal metrics may be shown on the graph 222, that the personal metrics may be associated with different time periods on the graph, and that the personal metrics may be expressed in different ways on the graph. With respect to the different types of personal metrics that may be shown on the graph 222, menu 230 illustrates at least four types of personal metrics that may be presented on the graph 222. Accordingly four options are possible on the menu 230, including an "Activity" option 232, a "Fitness" option 234, a "Nutrition" option 236, and a "Sleep" option 238. In the embodiment of FIG. 3C, if the user chooses the "Activity" option 232, personal metrics related to a user's steps are presented on the graph 222. If the user chooses the "Fitness" option 234, personal metrics related to a time of fitness minutes, or alternatively, calories spent are displayed on the graph 222. If the user chooses the "Nutrition" option 236, personal metrics related to calories consumed are displayed on the graph 222, or alternatively, a simplified nutrition indicator (as discussed below) is displayed on the graph 222. If the user chooses the "Sleep" option 238, personal metrics related to time of sleep, or quality of sleep, are displayed on the graph 222. In this manner, the user is provided with the ability to view any of various types of personal metrics using the health perception tool.

With respect to the personal metrics being associated with different time periods on the graph 222, menu 240 illustrates at least three different time associations for the personal metrics. Accordingly, three time options are shown on the menu 240, including the "Week" option 242, the "Month" option 244, and the "Year" option 246. If the user chooses the "Week" option 242, personal metrics related to a selected week of activity or health data will be shown on the graph 222, and particularly seven data points 224, one for each day of the week (e.g., Oct. 4-10, 2015). If the user chooses the "Month" option 244, personal metrics related to a selected month of activity or health data will be shown on the graph 222, and particularly four to six data points 224, with one data point for each of the weeks having at least one day of the week falling in the month (e.g., if October 2015 is selected, the five weeks falling between Sep. 27 and Oct. 31, 2015). In at least one alternative embodiment, if the user chooses the "Month" option 244, personal metrics for each day of the selected month of activity or health data may be shown on the graph 222 (e.g., 31 days of activity or health data for the month of October). If the user chooses the "Year" option 246, personal metrics related to a selected year of activity or health data will be shown on the graph 222, and particularly as many as twelve data points 224, one data point for each month of the year. In at least one alternative embodiment, if the user chooses the "Year" option 246, personal metrics for each month of a selected twelve month period may be shown on the graph 222 (e.g., twelve data points for the months between June 2014 and May 2015).

With respect to expressing personal metrics in different ways on the graph, the activity or health data may be processed in different ways to arrive at different personal metrics for the same activity or health data. For example, although the graph 222 of FIG. 3C expresses each personal metric data point 224 as a percentage as a goal, the personal metrics may be expressed differently, such as a total number of steps during the selected period of time, without any association with a goal. Similarly, depending on the user's option from the menu 230, personal metrics may be calculated from the activity or health data and may or may not be associated with a defined goal of the user. The system may automatically determine how personal metrics will be displayed (e.g., in association with a goal), or the user may select from a number of different options for personal metrics in the settings for the health perception tool (e.g., the user may choose to display personal metrics for activity defined by steps taken as total steps for a time period or a percentage of a defined goal). Processing of the activity or health data to arrive at the personal metrics and associated data points 224 may be accomplished using the processor 37 on the display device 30, or may occur remotely via a remote server in communication with the display device 30 (e.g., via the cloud).

With continued reference to FIG. 3C, the health perception portion 250 of the output screen 200 of the health perception tool is further configured to display health perception metrics on a health perception graph 252, the health perception metrics based on the health perception data input by the user and associated with some period of time. In the embodiment of FIG. 3C, the health perception graph 252 includes health perception metrics that are associated with the same period of time as the personal metrics on the first graph 222. In this embodiment, the health perception metrics are provided on a bar chart including a plurality of bars 254 positioned in relation to a vertical scale 255. The vertical scale 255 includes numbers that are associated with the numbers on the sliding scale 142 of the health perception prompt 140 (e.g., the vertical scale 255 includes numbers between 1 and 10). Each bar 254 has a height representing a value for the health perception metric, and these numbers are associated with the numbers on the sliding scale 142, or some fraction thereof, such as 6 or 6.5, depending on how the value is determined. Each bar 254 is also associated with one of a plurality of time periods, which time periods are the same as those shown on the x-axis 229 in association with the graph 222. While FIG. 3C shows the data points associated with health perception metrics provided as bars 254 in the graph 252, it will be appreciated that the data points may be provided in different forms, such as coordinate pairs similar to the data points 224 provided in the graph 222. Moreover, additional information may be provided by the bars 254. In the embodiment of FIG. 3C, the bars are colored (e.g., green or yellow) to indicate whether the user met his or her goal for the month associated with the bar. In other embodiments, additional colors or other indicia may be used in association with the bars 254 to display personal metrics related to the perceived health metrics for the associated period of time. For example, the bars may be one of four colors, a first color (e.g., red) to indicate that the user was far below the goal for a month, a second color (e.g., yellow) to indicate that the user was relatively close to the goal, a third color (e.g., green) to indicate that the user met the goal, and a fourth color (e.g., blue) to indicate that the user far surpassed the goal.

Various methods may be used to determine the health perception metrics displayed on the graph 252. For example, if each bar 254 on the graph 252 is associated with a single day, the value may be the final value of the health perception data entered by the user at the health perception prompt 140 for that day (e.g., "7"). Alternatively, the value may be a different entry by the user at a particular time of the day, or some combination of multiple entries of health perception data by the user over the course of the day, such as an average of all entries by the user during a day. Similarly, if each bar 254 on the graph 252 is associated with a period of time covering multiple days, such as a week or a month, the bar may represent an average number or other combination of health perception data entries by the user on the health perception prompt over that period of time. The term "average" as used herein refers to any of a number of different typical or representative numbers for a group of numbers, which may be calculated in any number of different ways, such as the mean, mode, median, etc.

Each health perception metric is displayed on the health perception graph 252 simultaneously and in conjunction with one of the personal metrics on the personal metrics graph 222. For example, in the embodiment of FIG. 3C, each data point 224 representing a personal metric is displayed on the display device 30 at the same time and on the same screen (e.g., dashboard screen 100) with each bar 254 representing a health perception metric. Also, in the embodiment of FIG. 3C, each data point 224 representing a personal metric is vertically aligned with one of the bars 254 representing a health perception metric, and these are both aligned with an associated month listed on the x-axis 229 of the graph 222. For example, dotted line 258 in FIG. 3C shows the personal metric and the health perception metric for the month of June 2015 aligned on the screen. While FIG. 3C shows one example of personal metrics displayed simultaneously and in conjunction with health perception metrics, it will be recognized that different methods of displaying personal metrics simultaneously and in conjunction with health perception metrics are possible. For example, personal metrics and health perception metrics may be combined on a single graph and listed side-by-side, presented on two graphs presented as a unitary overlay of the two graphs, presented different alignment of the data points between two graphs, presented as a different representation of the data points (e.g., coordinate pairs, bars, etc.), combined into unitary data points (e.g., each data point may convey multiple pieces of information such as a coordinate pair to represent one metric with a certain color to represent another metric), or any number of other methods for displaying the personal metrics simultaneously and in conjunction with the health perception metrics.

The disclosed system 10 provides a tool that integrates activity or health data for the user's daily life activities along with perceived health in order to provide the user with strategies to help the user feel better (e.g., eat well, sleep, exercise, etc., including the extent of a particular activity that may be required for the individual user to attain a desired level of health perception). In the disclosed embodiment, the personal metrics in graph 222 is shown simultaneously and in conjunction with the health perception metrics in graph 252, and this provides the user with a tool for determining whether any correlation exists between the personal metrics displayed on the screen and health perception metrics. For example, in FIG. 3C, when the user reviews the data on the personal metric graph 222 in conjunction with the health perception graph 252, the user can see that in the four months where the user perceived his or her health to be the best (i.e., the months of January, March, June and October), the user also met one or more of his or her activity or health goals for those months. At the same time, in the three of the four months in which the user perceived his or her health to be the worst, (i.e., April, May, July and August), the user fell well short of the activity or health goals for those months. In this manner, the user may understand that achievement of one or more activity or health goals has a correlation to the user's wellbeing. As also shown in FIG. 3C, the user may notice that the month in which the user had the highest health perception metric (i.e., the month of June), the user also exceeded his or her activity and/or health goals by the greatest amount (i.e., over 110% of goal achieved). In this manner, the user may see that he or she should consider increasing the monthly activity or health goal in an attempt to increase his or her sense of wellbeing. The system 10 provides the user with a tool that helps identify any significant correlation between how the user feels and any goals of the user, including goals related to physical activity, nutrition, or sleep. In this manner, the system is capable of making lifestyle recommendations to the user as the user analyzes his or her subjective feeling data over time in associate with activity or health data, including physical exercise, nutrition and sleep data.

In addition to the use of the two graphs 222 and 252, FIG. 3C also provides a further example of how personal metrics are provided simultaneously and in conjunction with health perception metrics. In particular, each bar 254 of the graph 252 not only has a height associated with a health perception metric (i.e., a number between one and ten), but also has a color association with a personal metric (i.e., a green color to indicate that the or a yellow color to indicate that the user did not meet his or her goal during the associated time period). For example, the bars 254 for the months of January, March, April, June, September and October are all shown with cross-hatching in FIG. 3C to represent a green color, indicating that the user met his or her goal during the associated month. On the other hand, the bars 254 form the months of February, May, July, and August are shown with no cross-hatching in FIG. 3C to represent a yellow color, indicating that the user did not meet his or her goal during the associated month. This allows the user to quickly see by looking only at the health perception portion 250 of the screen whether the user's perceived well-being was related to meeting a goal.

Figure 4:
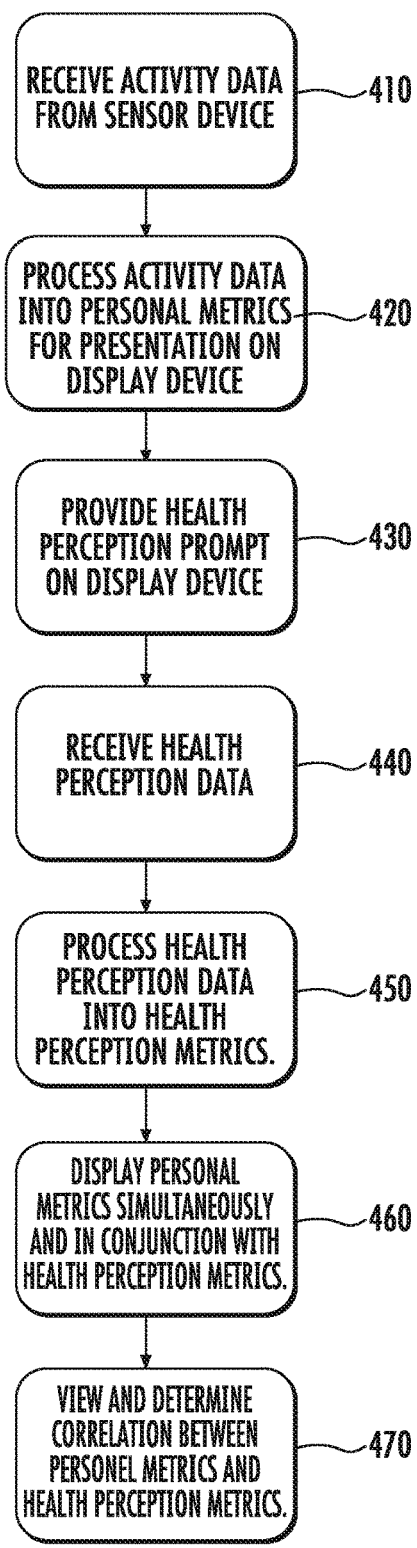
FIG. 4 is a logical flow diagram showing a method of presenting personal metrics and health perception metrics to a user.

With reference now to FIG. 4, the health tracking system 10 described herein provides for a method of providing activity or health data to a user using the health perception tool. An exemplary embodiment of this method is shown in FIG. 4. The method begins in step 410 wherein the health tracking system 10 receives activity data or other health data from a health monitoring device 20 carried by the user. Next, in step 420, the activity or health data received from the sensor device is processed for presentation on the display device 30 as personal metrics for the user, wherein each of the personal metrics associated with a period of time. Processing of the activity or health data collected by the sensor device may occur on the display device 30 or at a remote server in communication with the display device. In step 430, a health perception prompt is provided on the display device 30. The user inputs health perception data at the health perception prompt, and the health perception data is received by the system 10 at step 440. In step 450, the health perception data received by the display device is processed for presentation on the display device as health perception metrics for the user, wherein each of the health perception metrics associated with the period of time. The health perception tool associates personal metrics of the user with the health perception metrics and determines the appropriate data for presentation on the display screen based various system settings or preferences of the user. Then, in step 460, the health perception tool displays each of the personal metrics for the user on the display device simultaneously and in conjunction with each of the health perception metrics for the user. Thereafter, in step 470, the user views the personal metrics and health perception metrics. The user may determine whether a correlation exists between the personal metrics and the health perception metrics. Additionally, the user is able to derive certain understandings and possible alternations related to his or her lifestyle choices that may have an effect on his or her perceived health.

The foregoing are only a few examples of the understandings and suggestions that may be realized by a user upon review of the user's the personal metrics simultaneous and in conjunction with the user's health perception metrics. It will be recognized that various additional understandings and suggestions may be made to the user based on review of the user's the personal metrics being shown simultaneous and in conjunction with the user's health perception metrics. Moreover, when the user selects a different option in menu 230, different personal metrics may be shown in the personal metrics graph 222. One such example is discussed in further detail below with reference to FIGS. 5-9.

Nutrition Estimate Tool

Figure 5:
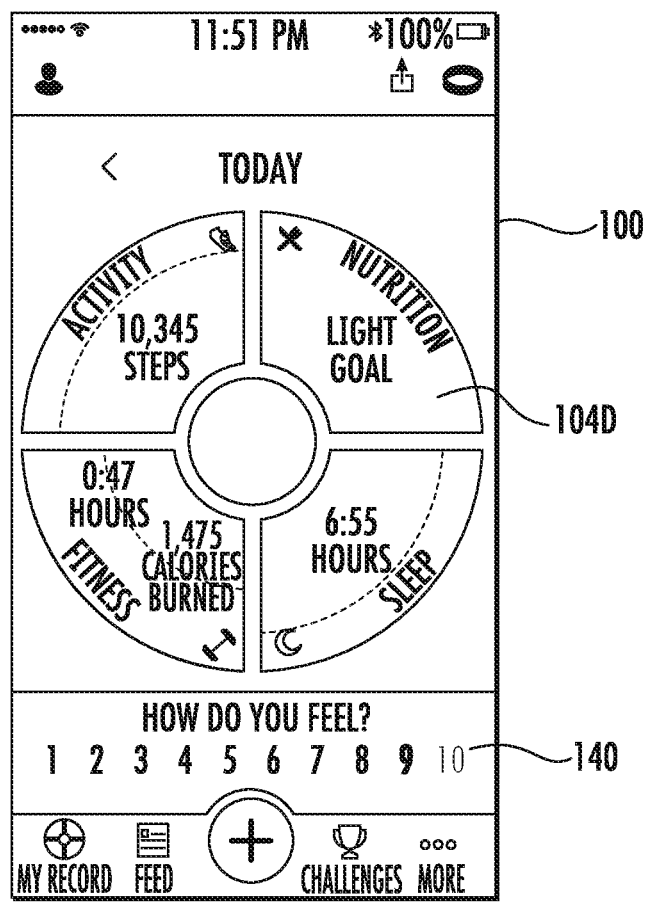
FIG. 5 is a plan view showing the display device of the activity tracking system of FIG. 1 including an alternative embodiment of a dashboard screen displayed on the display device, the screen a nutrition sector providing a link to a nutrition estimate tool.

With reference now to FIGS. 5-8, in at least one embodiment the activity or health tracking app includes a nutrition estimate tool. In various embodiments, the nutrition estimate tool may be included on the display device 30 along with the health perception tool. In other embodiments, the nutrition estimate tool and the health perception tool may be exclusive of one another and not used in association with the same activity or health tracking app or even the same display device. FIG. 5 shows an embodiment of the health tracking app wherein the dashboard screen 100 provides the user with access to both the health perception tool and the nutrition estimate tool. The user may access the health perception tool by selecting the health perception prompt 140. Alternatively, the user selects the nutrition sector 104D to access the nutrition estimate tool. In the embodiment of FIG. 5, the nutrition sector 104D shows that the user has a "light" goal for that particular day, indicating that the user's default goal is to consume a relatively light and nutritious amount for the day.

Figure 6:
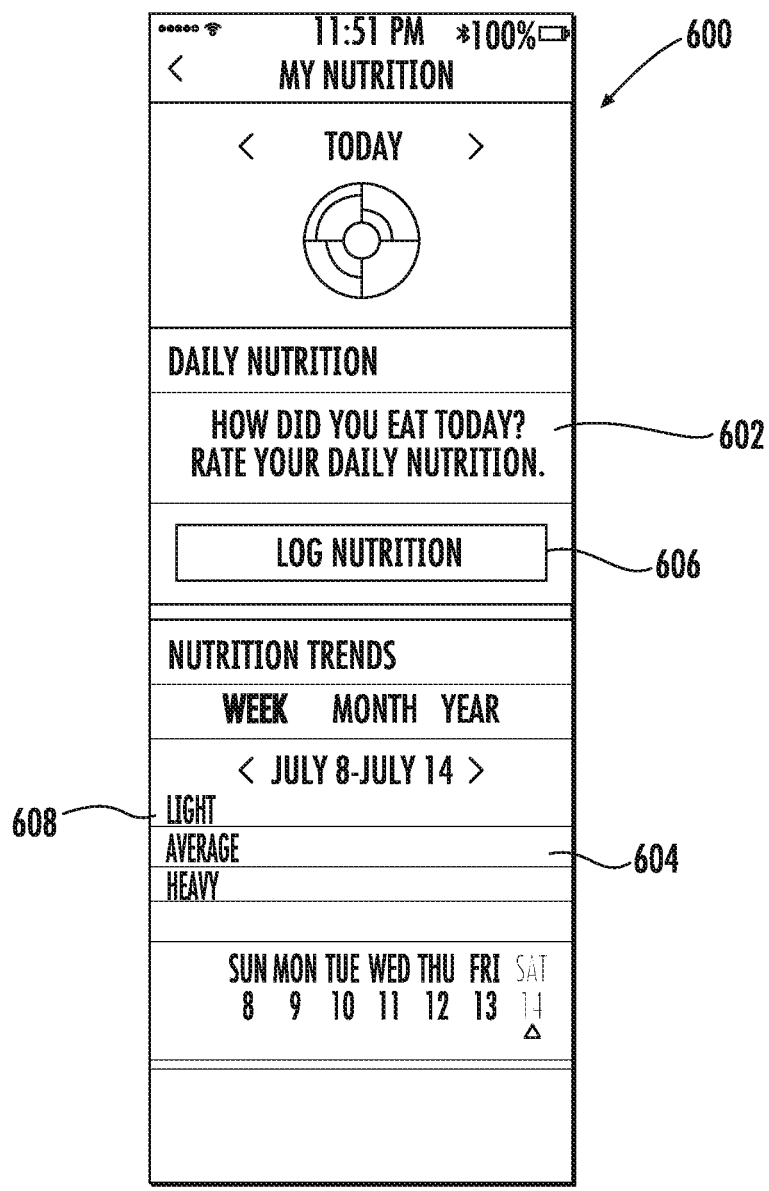
FIG. 6 is a plan view showing a daily nutrition page of the nutrition estimate tool of the activity tracking system of FIG. 1.

Upon selecting the nutrition sector 104D, the user is presented with a daily nutrition page 600 of the nutrition estimate tool, as shown in FIG. 6. The daily nutrition page 600 includes a nutrition logging portion 602 on an upper portion of the page, and a nutrition trends portion 604 on a lower portion of the page. The nutrition logging portion 602 on the upper portion of the page includes a "Log Nutrition" option 606. In the embodiment of FIG. 6, the nutrition logging portion asks the user "How did you eat today?" and invites the use to rate his or her daily nutrition using the "Log Nutrition" option 606. Selection of the "Log Nutrition" option takes the user to a log nutrition page 700, which includes a nutrition rating prompt 702 as explained in further detail below with reference to the embodiment of FIG. 7. The nutrition trends portion 604 on the lower portion of the page provides the user with a graph 608 of nutrition data collected by the system 10 over a period of time. In particular, as explained in further detail with reference to FIG. 8, nutrition estimate metrics based on nutrition consumption estimates entered by the user may be presented to the user on the graph 608.

Figure 7:
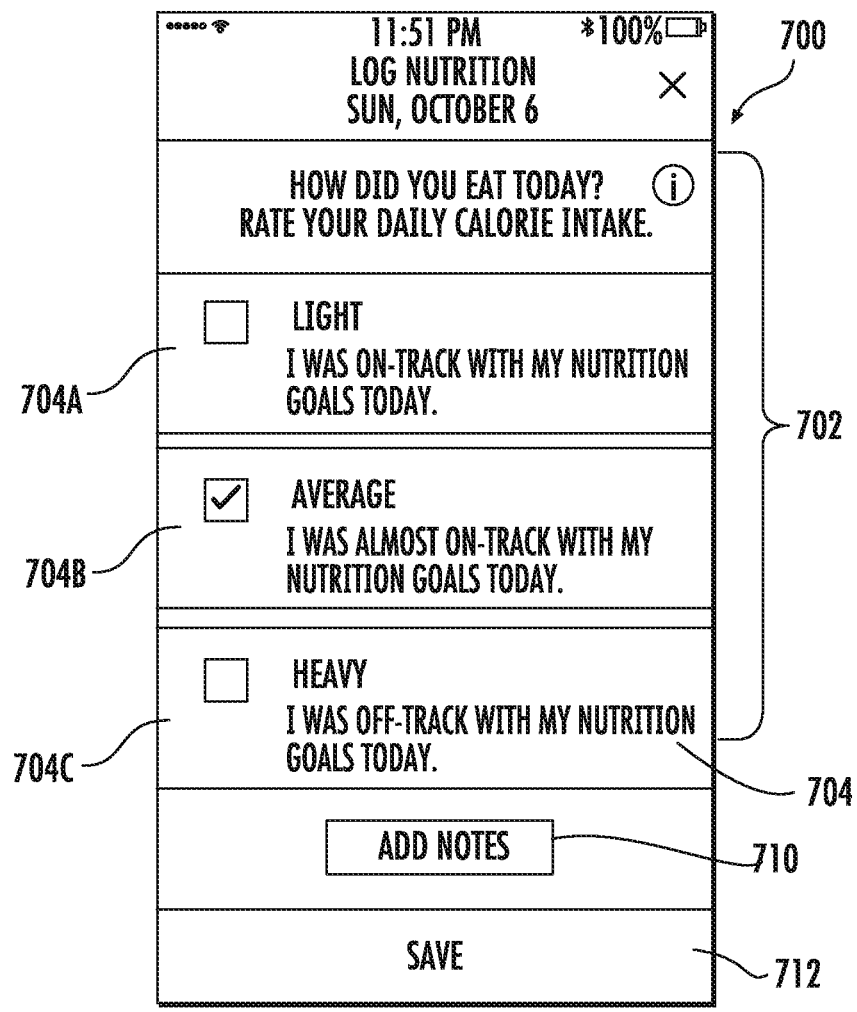
FIG. 7 is a plan view showing a nutrition rating prompt of the nutrition estimate tool of FIG. 6.

With reference now to FIG. 7, when the user selects the "Log Nutrition" option 606, the user is taken to the log nutrition page 700 and presented with the nutrition rating prompt 702. The nutrition rating prompt 702 includes a prompt question (e.g., "How did you eat today?") and a plurality of nutrition rating options 704. In the embodiment of FIG. 7, the nutrition rating prompt 702 includes three subjective nutrition rating options 704A-704C. Each of the nutrition rating options 704 allows the user to enter a subjective estimate of nutrition consumption for a defined period of time (e.g., a number of days, a number of weeks, or a number of months). The term "nutrition consumption estimate" as used herein refers to a user's approximation or judgement of his or her food consumption activity over a defined period of time based on the user's mental impressions of his or her food consumption activity over the defined period of time. In one embodiment, the "nutrition consumption estimate" is an approximation or judgement that is not based on a paper or electronic log of any particular foods or types of foods consumed by the user during the defined period of time, or any algorithms related thereto. Instead, a "nutrition consumption estimate" in this embodiment is a more general and subjective approximation or judgement made by the user based on the user's recollection of his or her food choices in aggregate over the course of the defined period of time (e.g., the day). A "nutrition consumption estimate" may be based on any of various factors, such as a user's food consumption goals, calories consumed, vitamin and mineral intake, etc. Similarly, the term "nutrition estimate metric" as used herein refers to any of various measures of nutrition estimates (e.g., in the embodiment of FIGS. 7-8, one of three values or ranges associated with one or more nutrition consumption estimate for the user). The nutrition rating prompt 702 advantageously enables the user to quickly and easily enter nutritional information without the need for the time-consuming and laborious task of manually entering specific foods and quantities of such foods consumed by the user.

In the exemplary embodiment of FIG. 7, each nutrition consumption estimate is dependent on a user-defined nutrition goal which has been set by the user (e.g., a goal set by the user in a settings portion of the activity or health tracking app) and utilizes a simplified nutritional estimate system. In one specific embodiment, the user has defined a nutrition goal to eat light and nutritious in order to lose or maintain weight. Based on this defined goal, the nutrition rating prompt 702 includes a "Light" nutrition rating option 704A, an "Average" nutrition rating option 704B, and a "Heavy" nutrition rating option 704C. If the user selects the "Light" nutrition rating option 704A, the user's nutrition consumption estimate is that he or she generally achieved his or her goal for the period of time (i.e., "I was on track with my nutrition goals today."). If the user selects the "Average" nutrition rating option 704B, the user's nutrition consumption estimate is that he or she was close, but did not quite achieve his or her goal for the period of time (i.e., "I was almost on track with my nutrition goals today."). If the "Heavy" nutrition rating option 704C is selected by the user, the user's nutrition consumption estimate is that he or she generally fell well short of his or her goal for the period of time (i.e., "I was off-track with my nutrition goals today.").

In view of the foregoing, it will be recognized that in at least one embodiment the nutrition rating options 704 presented to the user on the nutrition rating prompt 702 may be based on specific user goals. However, it will also be appreciated that the nutrition rating options 704 may be configured differently based on different goals, different estimates, or different periods of time. For example, in at least one exemplary embodiment, the user's goal may be to gain weight or eat a certain minimum number of calories for the day. In this embodiment, the nutrition consumption estimate for the "Heavy" nutrition rating option 704C may indicate that the user was "on-track" with nutrition goals for the day, while the "Light" nutrition rating option 704A may indicate that the user was "off-track" with nutrition goals for the day. Accordingly, it will be recognized that any of various goals may be defined by the user including (i) reduce calories and lose weight, (ii) maintain current weight, (iii) gain weight, (iv) eat a generally healthy and nutrition diet, (v) eat in a manner to address or manage a specific health condition (e.g., diabetic diet, heart healthy diet, etc.), (vi) eat a minimum number of calories, and (vii) eat a maximum number of calories. In yet another exemplary embodiment, the nutrition rating options 704 may be based on an estimate of calories consumed for the day, with each nutrition rating option 704 including a range of calories consumed for the day (e.g., 0-1000, 1000-2000, 2000-3000, 3000-4000, 4000+, etc.).

In yet another exemplary embodiment, the nutrition rating options may be based on a differently defined period of time, such as a sub-portion of a day (e.g., morning, afternoon or evening food consumption), or a period of days (e.g., a week or a month). In at least one embodiment, the user may be allowed to enter only a single nutrition rating option at the nutrition rating prompt for a single period of time. In such embodiment, the user may be blocked from the nutrition rating prompt or blocked from saving additional nutrition rating options until a predetermined portion of the period of time has elapsed following selection of a first nutrition rating option for the period of time. Alternatively, the system may save several user entries over a given day such as one after every meal. The several entries may be averaged over a day or may remain as independent entries for a given day.

With continued reference to FIG. 7, the lower portion of the log nutrition page 700 includes a user notes option 710 and a save option 712. By touching or otherwise selecting the user notes option 710, the user is presented with a notes box (not shown). The user may then enter text in the notes box (e.g., by typing or speaking) which will allow the user to note specific foods that were consumed and caused the user to choose the nutrition rating option 704 in the nutrition rating prompt 702. For example, if the user chooses the "Average" nutrition rating option 704B, the user may note the reasons for selecting this option (e.g., "Cheerios for breakfast, pasta for lunch, some M&Ms throughout the day, finished with a salmon salad and a glass of red wine"). Accordingly, it will be recognized that while the activity or health tracking system 10 does allow the user to manually log in particular foods consumed as notes or reasons selected of one of the simplified nutrition consumption estimates, the nutrition consumption estimate itself is based on the user's mental impressions of his or her food consumption activity over the defined period of time and not based on a paper or electronic log of any particular foods or types of foods consumed by the user during the defined period of time or any associated calorie or nutrition calculations, in this embodiment. Moreover, the notes entered by selecting the notes option 710 may or may not be nutrition related, and are generally offered for the user to review at a future time to assist the user in determining why he or she chose a particular nutrition rating option on a given day (e.g., "lots of fruits and veggies today," "too many sweets today," "ate like a pig over the holidays," etc.).

By selecting the save option 712, the user enters the nutrition rating option for the given period of time. If desired, the user may change the nutrition rating option by re-entering the nutrition rating prompt 702 during the same period of time and amending the selection. In at least one embodiment, the user may be allowed to enter only a single nutrition rating option at the nutrition rating prompt for a single period of time. In such embodiment, the user may be blocked from the nutrition rating prompt or blocked from saving additional nutrition rating options until a predetermined portion of the period of time has elapsed following entry of a first nutrition rating option for the period of time. Alternatively, on his or her most recent entry will be saved. In another embodiment, several entries for a single day may be saved.

Figure 8:
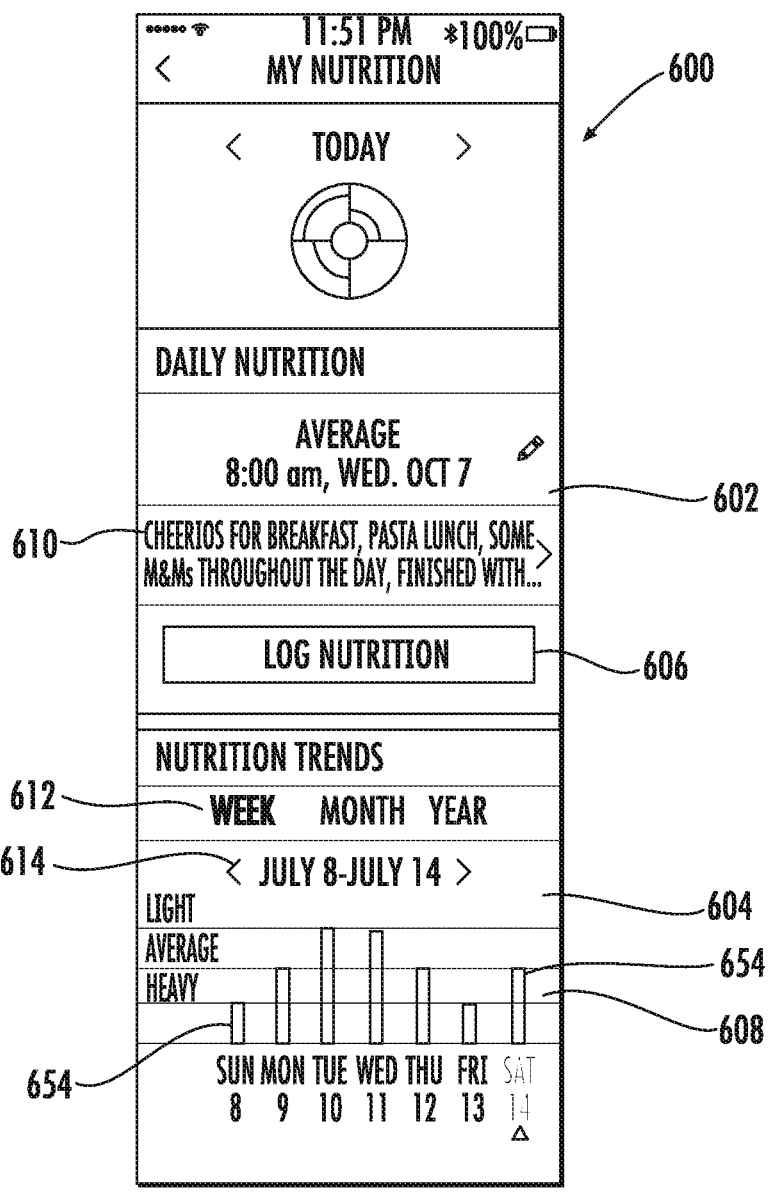
FIG. 8 is a plan view showing a nutrition estimate metrics page of the nutrition estimate tool of FIG. 6.

With reference now to FIG. 8, after the user saves one of the simplified nutrition rating options 704 as a nutrition consumption estimate, the user is returned to the daily nutrition page 600. In the embodiment of FIG. 8, the user saved a nutrition consumption estimate of "Average" and this is shown in the nutrition logging portion 602 on the upper portion of the page. Although a nutrition consumption estimate is already logged for the day, the user is still presented with the "Log Nutrition" option 606 in the event the user wishes to change the nutrition consumption estimate for the day. In the embodiment of FIG. 8, the user has also entered notes concerning the food consumed for the day, and these notes are displayed in a notes box 610.

The nutrition trends portion 604 on the lower portion of the page provides the user with a graph 608 of nutrition data collected by the system 10 in the form of nutrition estimate metrics provided over a period of time. Various periods of time to be viewed may be entered in the menu 612 (i.e., weeks, months or years). The user may scroll through contiguous periods of time using the date scrolling option 614. In the embodiment of FIG. 8, the user has selected to view nutrition estimate metrics for the week of July 8-July 14. Each nutrition estimate metric is displayed as a bar 654 on the graph 608. In this case, the height of each bar 654 represents a nutrition consumption estimate entered by the user on a given day (i.e., one of "Light," Average," or "Heavy"). The graph 608 includes each day of the week on the x-axis, and each of the possible nutrition consumption estimates on the y-axis. As shown in FIG. 8, during the week of July 8-July 14, the user's nutrition consumption estimate was "Light" for two days, "Average" for three days, and "Heavy" for two days. While the embodiment of FIG. 8 shows the nutrition estimate metrics as the same as nutrition consumption estimates for a period of time (i.e., the nutrition estimate metric for a day is the same as the nutrition rating option for the day), it will be appreciated that in other embodiments, the nutrition estimate metrics for the selected period of time may be calculated differently (e.g., the nutrition estimate metrics may be an average of nutrition rating options over the selected period of time). Also, it will be appreciated that additional data may be presented on the graph 608. For example, each bar 654 may have a different color associated with a different nutrition rating option. Alternatively each bar 654 may have a color associated with the user's health perception metric for the same day.

Using the graph 608 of the nutrition logging portion 602, the user is presented with a tool for determining and analyzing his or her eating trends. These trends may be determined based on the nutrition estimate metrics presented on the display screen, the nutrition estimate metrics based on the simplified nutrition rating options input by the user. For example, after scrolling a period of weeks, the user may recognize that he or she tends to eat more heavily on weekends than on weekdays. This provides the user with a tool for recognizing the source of eating problems and therefore a means for addressing the eating problems. Additionally, in at least one embodiment, the user's nutrition estimate metrics may be shown simultaneously and in conjunction with the user's health perception metrics, similar to the graph of FIG. 3C, but with the personal metrics graph 222 replaced by the nutrition estimate metrics graph 608. In this manner, the user may be alerted as to the effects that eating has on the user's perceived wellbeing.

The nutrition estimate tool is stored as instructions in the memory 38 of the display device 30 and is configured for execution by the processor 37. The nutrition estimate tool may be part of the activity or health tracking app, a separate application, and/or may be used in association with the activity or health tracking app; any of the foregoing may be stored as instructions in the memory 38 of the display device 30. In one embodiment, instructions to enable the herein disclosed functionality may be present on the device 30 at the time of manufacture or may be downloaded thereto via well-known mechanisms. As best shown in FIGS. 6-8 described above, execution of the health perception tool may result in display of the log nutrition page, the health perception prompt 702, as well as any of various other pages screens or prompts.

Figure 9:
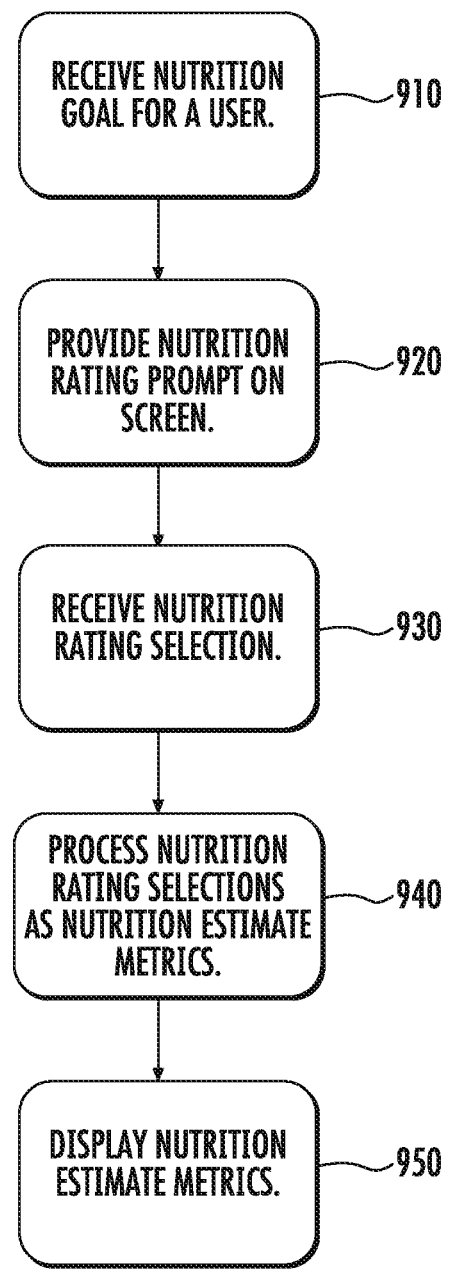
FIG. 9 is a logical flow diagram showing a method of presenting nutrition estimate metrics to a user.

The health tracking system 10 described herein provides for a method of providing activity or health data to a user using the nutrition estimate tool. An exemplary embodiment of this method is shown in FIG. 9. The method begins in step 910 wherein the system receives a nutrition goal for a user at the user's personal electronic device. In step 920, a simplified nutrition rating prompt is provided for the user on a display screen of a personal electronic device. The simplified nutrition rating prompt includes a plurality of nutrition rating options, each of the nutrition rating options providing a nutrition consumption estimate associated with a period of time. In step 930, the system receives one or more of selected nutrition rating options from the user during the period of time at the nutrition rating prompt. Thereafter, in step 940, the system processes the one or more selected nutrition rating options from the user for presentation on the personal electronic device as nutrition estimate metrics for the user, each of the nutrition estimate metrics associated with the period of time. In step 950, the nutrition estimate metrics for the user are displayed on the display screen of the personal electronic device. I will be recognized that the method of FIG. 9 may be used separately from, in conjunction with, or in addition to the method of FIG. 4, described above. For example, the steps of FIG. 9 may be performed simultaneously with the steps of FIG. 4. Moreover, the nutrition estimate metrics of FIG. 8 may be shown simultaneously and in conjunction with the personal metrics or the health perception metrics described in association with FIGS. 3A-3C.

The foregoing method may be accomplished with the assistance of a computer program, such as the activity or health tracking app described above, stored in the memory 38 and executed by the processor 37 of the display device. The above described system and method solves a technological problem common in industry practice related to effective and efficient presentation of health data to a user. Moreover, the above-described system and method improves the functioning of the computer/device by allowing activity and health data to be effectively communicated to the user along with perceived health data on a single display screen. The system and method also allows the user to easily view personal metrics and perceived health metrics and derive lifestyle patterns from this data.

Portions of the system and methods described herein may be implemented using one or more programs or suitable software code, such as the activity or health tracking app described above, that may reside within the memory as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer readable medium can be, by way of example, only but not by limitation, an electronic, magnetic, optical, electromagnetic, infrared, or semiconductor system, apparatus, system, device, or computer memory. The computer readable medium may include multiple computer readable media storing computer executable instructions, such as in a distributed system or instructions stored across an array. A "non-transient computer-readable medium" may be any type of data storage medium that can store computer instructions, including, but not limited to the memory devices discussed above.

The above described system and method solves a technological problem common in industry practice related to effective and efficient presentation of health data to a user for analysis and consideration by the user. Moreover, the above-described system and method improves the functioning of the computer device by causing activity, health, and/or nutritional data to be easily presented to a user in a health tracking system, while also allowing the user to manipulate the activity, health, and/or nutritional data or otherwise make use of the nutritional data in the manner that he or she sees fit. In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system including a health perception tool, a nutrition estimate tool, a display device, and associated screens thereof has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A personal electronic device configured to provide health-related information to a user, the personal electronic device comprising:
   a receiver configured to receive health data obtained by a sensor device and/or manually entered by the user;
   a processor configured to execute a computer program comprising a plurality of instructions which are configured to, when executed, cause the processor to process said received health data into a plurality of personal metrics; and
   an interactive display screen configured to:
      receive a nutrition goal from the user;
      display the plurality of personal metrics, each of the plurality of personal metrics being associated with a period of time, wherein the period of time is at least one day;
      display a nutrition rating prompt comprising a plurality of simplified nutrition rating options, each of the simplified nutrition rating options providing a nutrition consumption estimate based on a subjective observation of the user and associated with the period of time, wherein the nutrition rating options are presented on the display screen during the day both before and after a predetermined portion of the period of time has elapsed;
      receive a selection of at least one of the simplified nutrition rating options by the user at the nutrition rating prompt after the predetermined portion of the period of time has elapsed;
      block the user from selecting one or more of the simplified nutrition rating options at the nutrition rating prompt before the predetermined portion of the period of time has elapsed;
      display a notes option in association with the nutrition rating prompt;
      after receiving the selection of the at least one of the simplified nutrition rating options, receive a selection of the notes option; and
      in response to the selection of the notes option, provide the user with a text tool allowing the user to input a text description of food consumption for the period of time;
   wherein the processor is further configured to generate nutrition estimate metrics based on the selection of the at least one of the simplified nutrition rating options by the user and cause the nutrition estimate metrics to be displayed on the interactive display screen in association with the nutrition goal for the user after the predetermined portion of the period of time has elapsed;
   wherein the nutrition rating prompt provides the user with three simplified nutrition rating options, each of the three simplified nutrition rating options proving a nutrition consumption estimate associated with the nutrition goal for the user; and
   wherein a first of the three simplified nutrition rating options indicates that the user achieved the nutrition goal for the period of time, a second of the three simplified nutrition rating options indicates that the user nearly achieved the nutrition goal for the period of time, and a third of the three simplified nutrition rating options indicates that the user did not achieve the nutrition goal for the period of time.

2. The personal electronic device of claim 1 wherein the nutrition goal is a maximum calorie consumption goal, a minimum calorie consumption goal, or a healthy eating goal.

3. The personal electronic device of claim 1 wherein the notes option is provided as a button adjacent to the nutrition rating prompt on the interactive display screen.

4. The personal electronic device of claim 1 wherein the sensor device is housed remotely from the personal electronic device and configured to be carried by the user, the sensor device including at least one sensor configured to obtain the health data for the user.

5. The personal electronic device of claim 4 wherein the health data and the nutrition estimate metrics are presented in sector form on the display screen.

6. The personal electronic device of claim 1 further comprising a health perception prompt on the personal electronic device, the personal electronic device further configured to receive health perception data input by the user at the health perception prompt and display health perception metrics on the display screen, each of the health perception metrics based on the health perception data received at the personal electronic device and associated with the period of time.

7. The personal electronic device of claim 6 wherein the personal electronic device is further configured to display each of the nutrition estimate metrics simultaneously and in conjunction with each of the health perception metrics.

8. The personal electronic device of claim 1 wherein the period of time is one of a number of days, a number of weeks, or a number of months.

9. The personal electronic device of claim 1 wherein the plurality of personal metrics include at least one of steps and time of sleep.

10. The personal electronic device of claim 1 wherein the interactive display screen is further configured to:
  receive from the user the text description of food consumption for the period of time; and
  display the text description of food consumption for the period of time on the display screen in association with the nutrition estimate metrics and the nutrition goal of the user.

11. A method of presenting health data to a user, the method comprising:
  receiving a nutrition goal for a user at a personal electronic device;
  displaying a nutrition rating prompt on a display screen of the personal electronic device, the nutrition rating prompt including a plurality of nutrition rating options, each of the nutrition rating options providing a subjective nutrition consumption estimate associated with a period of time, wherein the period of time is at least one day;
  preventing selection of one or more of the nutrition rating options at the nutrition rating prompt displayed on the display screen until a predetermined portion of the at least one day has elapsed;
  receiving a selection of one of the nutrition rating options displayed on the display screen from the user after the predetermined portion of the at least one day has elapsed;
  processing the selection of the one of the nutrition rating options for presentation on the personal electronic device as nutrition estimate metrics for the user, each of the nutrition estimate metrics associated with the period of time; and
  displaying the nutrition estimate metrics for the user in association with the nutrition goal of the user on the display screen of the personal electronic device, wherein the nutrition goal is represented by a shape and the nutrition estimate metrics are represented by an amount of fill within the shape;
  wherein the nutrition rating prompt provides the user with three qualitative nutrition rating options, each of the three qualitative nutrition rating options providing a subjective nutrition consumption estimate associated with the period of time, wherein processing the selection of the one of the qualitative nutrition rating options includes associating the one of the qualitative nutrition rating options with a corresponding quantitative nutrition estimate metric relative to a nutrition goal, wherein a first of the three nutrition rating options corresponds to the user achieving the nutrition goal for the period of time, a second of the three nutrition rating options corresponds to the user nearly achieving the nutrition goal for the period of time, and a third of the three nutrition rating options corresponds to the user not achieving the nutrition goal for the period of time.

12. The method of claim 11 further comprising:
  receiving health perception data input by the user on the personal electronic device;
  processing the health perception data received by the personal electronic device for presentation on the display screen as health perception metrics for the user, each of the health perception metrics associated with the period of time; and
  displaying each of the health perception metrics for the user simultaneously and in conjunction with each of the nutrition estimate metrics for the user on the display screen of the personal electronic device.

13. The method of claim 11 further comprising:
  receiving biometric health data from a sensor device carried by the user at the personal electronic device; and
  processing the biometric health data received from the sensor device for presentation on the display screen as personal metrics for the user, each of the personal metrics associated with the period of time.

14. A non-transient computer readable medium containing instructions for controlling a personal electronic device by:
  receiving a nutrition goal for a user at the personal electronic device;
  displaying a nutrition rating prompt on a display screen of the personal electronic device, the nutrition rating prompt including a plurality of selectable nutrition rating options, each of the nutrition rating options providing a nutrition consumption estimate associated with a period of time, wherein the period of time is at least one day;
  preventing the user from selecting one or more of the nutrition rating options at the nutrition rating prompt until a predetermined portion of the at least one day has elapsed;
  receiving a selection by a user of one or more of the selectable nutrition rating options during the period of time and after the predetermined portion of the at least one day has elapsed;
  displaying a notes option on the display screen in association with the nutrition rating prompt;
  receiving a selection of the notes option from the user;
  in response to the selection of the notes option, displaying a text tool allowing the user to input a text description of food consumption during the at least one day;
  processing the selection of the one or more of the selectable nutrition rating options for presentation on the personal electronic device as nutrition estimate metrics for the user, each of the nutrition estimate metrics associated with the period of time; and displaying the nutrition estimate metrics for the user in association with the nutrition goal of the user on the display screen of the personal electronic device, wherein the nutrition goal is represented by a shape and the nutrition estimate metrics are represented by a boundary within the shape;

wherein the nutrition rating prompt provides the user with three selectable nutrition rating options, each of the three selectable nutrition rating options providing a nutrition consumption estimate associated with the nutrition goal for the user, wherein a first of the three selectable nutrition rating options indicates that the user achieved the nutrition goal for the period of time, a second of the three selectable nutrition rating options indicates that the user nearly achieved the nutrition goal for the period of time, and a third of the three selectable nutrition rating options indicates that the user did not achieve the nutrition goal for the period of time.

15. The computer readable medium of claim 14 further comprising instructions for controlling a personal electronic device by:

receiving health perception data input by the user on the personal electronic device;

processing the health perception data received by the personal electronic device for presentation on the display screen as health perception metrics for the user, each of the health perception metrics associated with the period of time; and displaying each of the health perception metrics for the user simultaneously and in conjunction with each of the nutrition estimate metrics for the user on the display screen of the personal electronic device.

* * * * *